(12) United States Patent
Bates et al.

(10) Patent No.: US 10,393,737 B2
(45) Date of Patent: *Aug. 27, 2019

(54) SAMPLE ASSEMBLY WITH AN ELECTROMAGNETIC FIELD TO ACCELERATE THE BONDING OF TARGET ANTIGENS AND NANOPARTICLES

(71) Applicant: International Business Machines Corporation, Armonk, NY (US)

(72) Inventors: Allen K. Bates, Tucson, AZ (US); Nils Haustein, Soergenloch (DE); Stephen L. Schwartz, Tucson, AZ (US); Anna W. Topol, Clifton Park, NY (US); Daniel J. Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 313 days.

This patent is subject to a terminal disclaimer.

(21) Appl. No.: 15/169,340

(22) Filed: May 31, 2016

(65) Prior Publication Data

US 2016/0274099 A1   Sep. 22, 2016

Related U.S. Application Data

(63) Continuation of application No. 13/616,855, filed on Sep. 14, 2012, now Pat. No. 9,435,800.

(51) Int. Cl.
*G01N 33/543* (2006.01)
*G01N 15/10* (2006.01)
(Continued)

(52) U.S. Cl.
CPC . *G01N 33/54386* (2013.01); *G01N 33/54326* (2013.01); *G01N 33/54333* (2013.01);
(Continued)

(58) Field of Classification Search
None
See application file for complete search history.

(56) References Cited

U.S. PATENT DOCUMENTS

| 2,376,965 A | 5/1945 | Alf |
| 2,948,624 A | 8/1960 | Watson et al. |

(Continued)

FOREIGN PATENT DOCUMENTS

| CN | 1454851 A | 11/2003 |
| CN | 1783219 A | 6/2006 |

(Continued)

OTHER PUBLICATIONS

Non-Final Office Action from U.S. Appl. No. 14/869,734, dated Jun. 6, 2018.
(Continued)

*Primary Examiner* — Rebecca L Martinez
(74) *Attorney, Agent, or Firm* — Zilka-Kotab, P.C.

(57) ABSTRACT

Described are embodiments of an invention for a sample assembly with an electrical conductor for detection of the antigens by electromagnetic read heads. In one embodiment, a sample assembly includes: a substrate; one or more base layers above the substrate; an outer layer above the substrate; a plurality of sample trenches formed in the outer layer, each sample trench being characterized by an upper surface, a bottom surface, and a longitudinal axis; an electrical conductor disposed in the substrate, the electrical conductor being configured to generate an electromagnetic field in proximity to the plurality of sample trenches to enhance nanoparticle movement toward the bottom surface of the plurality of sample trenches; and at least one alignment trench formed above the substrate, each alignment trench having a longitudinal axis substantially parallel to a longitudinal axis of at least one of the sample trenches.

19 Claims, 11 Drawing Sheets

(51) Int. Cl.
  *B82Y 15/00* (2011.01)
  *B82Y 5/00* (2011.01)
(52) U.S. Cl.
  CPC . *G01N 33/54346* (2013.01); *G01N 33/54353* (2013.01); *G01N 33/54366* (2013.01); *G01N 33/54393* (2013.01); *B82Y 5/00* (2013.01); *B82Y 15/00* (2013.01); *G01N 15/1031* (2013.01)

(56) References Cited

U.S. PATENT DOCUMENTS

| | | | |
|---|---|---|---|
| 3,823,276 | A | 7/1974 | Maslowski et al. |
| 4,062,047 | A | 12/1977 | Scull |
| 4,292,920 | A | 10/1981 | Smith et al. |
| 4,708,931 | A | 11/1987 | Christian |
| 5,005,096 | A | 4/1991 | Krounbi et al. |
| 5,146,004 | A | 9/1992 | Morris et al. |
| 5,189,571 | A | 2/1993 | Murphy et al. |
| 5,206,159 | A | 4/1993 | Cohen et al. |
| 5,206,590 | A | 4/1993 | Dieny et al. |
| 5,331,493 | A | 7/1994 | Schwarz |
| 5,376,965 | A | 12/1994 | Nagasaki et al. |
| 5,452,164 | A | 9/1995 | Cole et al. |
| 5,465,185 | A | 11/1995 | Heim et al. |
| 5,615,065 | A | 3/1997 | Cheung |
| 5,661,039 | A | 8/1997 | Kung et al. |
| 5,689,384 | A | 11/1997 | Albrecht et al. |
| 5,689,394 | A | 11/1997 | Esser et al. |
| 5,736,349 | A | 4/1998 | Sasaki et al. |
| 5,764,567 | A | 6/1998 | Parkin |
| 5,840,889 | A | 11/1998 | Cavalieri et al. |
| 5,863,507 | A | 1/1999 | James |
| 5,922,537 | A | 7/1999 | Ewart et al. |
| 5,948,624 | A | 9/1999 | Rothschild et al. |
| 5,965,375 | A | 10/1999 | Valkirs |
| 6,013,531 | A | 1/2000 | Wang et al. |
| 6,021,013 | A | 2/2000 | Albrecht et al. |
| 6,027,946 | A | 2/2000 | Weitschies et al. |
| 6,282,051 | B1 | 8/2001 | Albrecht et al. |
| 6,320,719 | B1 | 11/2001 | Albrecht et al. |
| 6,432,346 | B1 | 8/2002 | Hall |
| 6,462,904 | B1 | 10/2002 | Albrecht et al. |
| 6,493,172 | B1 | 12/2002 | Morris et al. |
| 6,548,311 | B1 | 4/2003 | Knoll |
| 6,643,084 | B1 | 11/2003 | Andrew et al. |
| 6,736,978 | B1 | 5/2004 | Porter et al. |
| 6,770,489 | B1 | 8/2004 | Enpuku |
| 6,962,685 | B2 | 11/2005 | Sun |
| 7,153,366 | B1 | 12/2006 | Chen et al. |
| 7,342,738 | B1 | 3/2008 | Anderson et al. |
| 7,556,863 | B2 | 7/2009 | Beming et al. |
| 7,639,448 | B2 | 12/2009 | Haustein et al. |
| 7,639,488 | B2 | 12/2009 | Tu |
| 7,649,708 | B2 | 1/2010 | Winarski et al. |
| 7,649,709 | B2 | 1/2010 | Winarski et al. |
| 7,679,858 | B2 | 3/2010 | Winarski et al. |
| 7,960,184 | B2 | 6/2011 | Morozov et al. |
| 8,694,280 | B2 | 4/2014 | Awezec et al. |
| 9,034,660 | B2 | 5/2015 | Boday et al. |
| 9,081,004 | B2 | 7/2015 | Boday et al. |
| 9,304,130 | B2 | 4/2016 | Boday et al. |
| 9,435,800 | B2 | 9/2016 | Bates et al. |
| 10,132,804 | B2 | 11/2018 | Bates et al. |
| 10,317,398 | B2 | 6/2019 | Boday et al. |
| 2002/0001960 | A1 | 1/2002 | Wu et al. |
| 2002/0030044 | A1 | 3/2002 | Brown |
| 2002/0119470 | A1 | 8/2002 | Nerenberg et al. |
| 2002/0174453 | A1 | 11/2002 | Daniell et al. |
| 2003/0077616 | A1 | 4/2003 | Lomas |
| 2003/0077642 | A1 | 4/2003 | Fritsch et al. |
| 2003/0186465 | A1 | 10/2003 | Kraus et al. |
| 2004/0002125 | A1 | 1/2004 | Gombrich et al. |
| 2004/0061968 | A1 | 4/2004 | Fukushima et al. |
| 2004/0080855 | A1 | 4/2004 | Tsuchiya et al. |
| 2004/0132220 | A1 | 7/2004 | Fish |
| 2004/0166508 | A1 | 8/2004 | Pawlak et al. |
| 2004/0219361 | A1 | 11/2004 | Cui et al. |
| 2004/0219631 | A1 | 11/2004 | Yokozeki et al. |
| 2005/0087000 | A1 | 4/2005 | Coehoorn et al. |
| 2005/0100930 | A1 | 5/2005 | Wang et al. |
| 2006/0020371 | A1 | 1/2006 | Ham et al. |
| 2006/0040273 | A1 | 2/2006 | Chaiken et al. |
| 2006/0051237 | A1 | 3/2006 | Wang et al. |
| 2006/0128035 | A1 | 6/2006 | Coehoorn et al. |
| 2006/0216696 | A1 | 9/2006 | Goguen |
| 2007/0054154 | A1 | 3/2007 | Leu |
| 2007/0115578 | A1 | 5/2007 | Winarski et al. |
| 2007/0146715 | A1 | 6/2007 | Potyrailo et al. |
| 2007/0146925 | A1 | 6/2007 | Haustein et al. |
| 2008/0012119 | A1 | 1/2008 | Otremba et al. |
| 2008/0036450 | A1 | 2/2008 | Kahlman et al. |
| 2008/0206104 | A1 | 8/2008 | Prins et al. |
| 2008/0226917 | A1 | 9/2008 | Zhong et al. |
| 2009/0021856 | A1 | 1/2009 | Winarski et al. |
| 2009/0027801 | A1 | 1/2009 | Winarski et al. |
| 2009/0047520 | A1 | 2/2009 | Lee et al. |
| 2009/0066318 | A1 | 3/2009 | Kahlman et al. |
| 2009/0072815 | A1 | 3/2009 | Kahlman et al. |
| 2009/0104707 | A1 | 4/2009 | Wang et al. |
| 2009/0152657 | A1 | 6/2009 | Suh et al. |
| 2009/0170212 | A1 | 7/2009 | Van Der Wijk et al. |
| 2009/0212768 | A1 | 8/2009 | Llandro et al. |
| 2009/0243594 | A1 | 10/2009 | Kahlman |
| 2009/0268325 | A1 | 10/2009 | Iben et al. |
| 2009/0273857 | A1 | 11/2009 | Iben et al. |
| 2009/0314066 | A1 | 12/2009 | Nieuwenhuis et al. |
| 2010/0017922 | A1 | 1/2010 | Shin et al. |
| 2010/0021708 | A1 | 1/2010 | Kong et al. |
| 2010/0093119 | A1 | 4/2010 | Shimizu |
| 2010/0147003 | A1 | 6/2010 | Ueda et al. |
| 2011/0053289 | A1 | 3/2011 | Lowe et al. |
| 2011/0070440 | A1 | 3/2011 | Linhardt et al. |
| 2011/0076670 | A1 | 3/2011 | Boday et al. |
| 2011/0076726 | A1 | 3/2011 | Lakey et al. |
| 2011/0076782 | A1 | 3/2011 | Awezec et al. |
| 2011/0077869 | A1 | 3/2011 | Boday et al. |
| 2011/0077902 | A1 | 3/2011 | Awezec et al. |
| 2011/0262955 | A1 | 10/2011 | Licher et al. |
| 2011/0293940 | A1 | 12/2011 | Tokoro et al. |
| 2012/0157330 | A1 | 6/2012 | Boday et al. |
| 2012/0164717 | A1 | 6/2012 | Irudayaraj |
| 2012/0280675 | A1 | 11/2012 | Berman et al. |
| 2012/0283976 | A1 | 11/2012 | Berman et al. |
| 2014/0080118 | A1 | 3/2014 | Bates et al. |
| 2016/0018392 | A1 | 1/2016 | Boday et al. |
| 2016/0223533 | A1 | 8/2016 | Boday et al. |
| 2016/0274102 | A1 | 9/2016 | Bates et al. |

FOREIGN PATENT DOCUMENTS

| | | |
|---|---|---|
| CN | 1967660 A | 5/2007 |
| CN | 101509919 A | 8/2009 |
| CN | 101558313 A | 10/2009 |
| CN | 101632018 A | 1/2010 |
| EP | 2073016 A1 | 6/2009 |
| WO | 2005010542 A2 | 2/2005 |
| WO | 2006047840 A1 | 5/2006 |
| WO | 2008102218 A1 | 8/2008 |
| WO | 2009039437 A1 | 3/2009 |
| WO | 2009083856 A2 | 7/2009 |
| WO | 2009157739 A2 | 12/2009 |

OTHER PUBLICATIONS

Boday et al., U.S. Appl. No. 12/970,837, filed Dec. 16, 2010.
Restriction Requirement from U.S. Appl. No. 12/970,837, dated Jan. 29, 2013.
Non-Final Office Action from U.S. Appl. No. 12/970,837, dated May 10, 2013.
Final Office Action from U.S. Appl. No. 12/970,837, dated Nov. 22, 2013.

(56) References Cited

OTHER PUBLICATIONS

Notice of Allowance from U.S. Appl. No. 12/970,837, dated Jan. 8, 2015.
Bates et al., U.S. Appl. No. 13/616,855, filed Sep. 14, 2012.
Non-Final Office Action from U.S. Appl. No. 13/616,855, dated Jun. 4, 2013.
Non-Final Office Action from U.S. Appl. No. 13/616,855, dated Dec. 30, 2013.
Final Office Action from U.S. Appl. No. 13/616,855, dated Jul. 24, 2014.
Office Action from German Application No. 112011104401.1, dated May 13, 2015.
Chinese Office Action from Application No. 201180060053.7 dated Jun. 27, 2014.
International Search Report and Written Opinion from International Application No. PCT/EP2011/070578, dated Mar. 19, 2012.
Awezec et al., U.S. Appl. No. 12/888,394, filed Sep. 22, 2010.
Awezec et al., U.S. Appl. No. 12/888,403, filed Sep. 22, 2010.
Boday et al., U.S. Appl. No. 12/888,408, filed Sep. 22, 2010.
Boday et al., U.S. Appl. No. 12/888,388, filed Sep. 22, 2010.
Crowther, J., "The ELISA Guidebook," Humana Press, Totowa, New Jersey, 2001, pp. 1-425.
Fox et al., "Tear and Serum Antibody Levels in Ocular Herpetic Infection: Diagnostic Precision of Secretory IgA," British Journal of Ophthalmology, vol. 70, 1986, pp. 584-588.
Liu et al., "Discrimination of specific and non-specific bindings by dielectrophoretic repulsion in on-chip magnetic bio-assays," Journal of Biosensors and Bioelectronics, No. 24, 2009, pp. 2294-2297.
Llandro et al., "Magnetic biosensor technologies for medical applications: a review," Med. and Biol. Eng. and Computing, Springer Berlin, Jun. 15, 2010, 22 Pages.
Millen et al., "Giant Magenetoresistive Sensors. 2. Detection of Biorecognition Events at Self-Referencing and Magnetically Tagged Arrays", Analytical Chemistry, vol. 80, No. 21, pp. 7940-7946, Nov. 1, 2008.
Nordling et al., "Giant Magnetoresistance Sensors. 1. Internally Calibrated Readout of Scanned Magnetic Arrays," Anal. Chem., vol. 80, 2008, pp. 7930-7939.
Osterfeld et al., "Multiplex protein assays based on real-time magnetic nanotag sensing," PNAS, vol. 105, No. 52. Dec. 30, 2008, pp. 20637-20640.
Piedade et al., "A New Hand-Held Microsystem Architecture for Biological Analysis," IEEE Trans. on Circuits and Systems—I: Regular Papers, vol. 53, No. 11, Nov. 2006, pp. 2384-2395.
Schuurs et al., "Enzyme-Immunoassay," Clini Chim Acta, vol. 81, 1977, pp. 1-40.
Shen et al., "Detection of DNA labeled with magnetic nanoparticles using MgO-based magnetic tunnel junction sensors," Journal of Applied Physics, vol. 103, 2008, pp. 07 A306-1-07 A306-3.
Yammamoto et al., "Active immobilization of biomolecules on a hybrid three-dimensional nanoelectrode by dielectrophoresis for single-biomolecule study," Nanotechnology, vol. 18,2007,495503, pp. 1-7.
Non-Translated Foreign Document WO2009157739.
Boday et al., U.S. Appl. No. 14/869,734, filed Sep. 29, 2015.
Non-Final Office Action from U.S. Appl. No. 13/616,855, dated Nov. 20, 2015.
Notice of Allowance from U.S. Appl. No. 12/970,837, dated Jan. 7, 2016.
Supplemental Notice of Allowance from U.S. Appl. No. 12/970,837, dated Mar. 1, 2016.
Notice of Allowance from U.S. Appl. No. 13/616,855, dated Mar. 15, 2016.
Boday et al., U.S. Appl. No. 15/096,175, filed Apr. 11, 2016.
Supplemental Notice of Allowance from U.S. Appl. No. 13/616,855, dated Apr. 19, 2016.
Non-Final Office Action from U.S. Appl. No. 15/169,479, dated Jan. 18, 2018.
Bates et al., U.S. Appl. No. 15/169,479, filed May, 31, 2016.
Awezec et al., U.S. Appl. No. 61/246,329, filed Sep. 28, 2009.
Final Office Action from U.S. Appl. No. 13/099,360, dated Feb. 25, 2014.
Non-Final Office Action from U.S. Appl. No. 13/099,360, dated Oct. 1, 2013.
Notice of Allowance from U.S. Appl. No. 13/099,358, dated Sep. 15, 2014.
Notice of Allowance from U.S. Appl. No. 13/099,360, dated Jun. 4, 2014.
Restriction Requirement from U.S. Appl. No. 13/099,358, dated Jun. 20, 2014.
Advisory Action from U.S. Appl. No. 12/888,388, dated Jul. 25, 2013.
Final Office Action from U.S. Appl. No. 12/888,388, dated May 9, 2013.
Notice of Allowance from U.S. Appl. No. 12/888,388, dated Jan. 12, 2015.
Non-Final Office Action from U.S. Appl. No. 12/888,388, dated Jan. 7, 2013.
Restriction Requirement from U.S. Appl. No. 12/888,388, dated Aug. 28, 2012.
Non-Final Office Action from U.S. Appl. No. 12/888,394, dated Oct. 7, 2013.
Restriction Requirement from U.S. Appl. No. 12/888,394, dated Dec. 10, 2012.
Final Office Action from U.S. Appl. No. 12/888,403, dated Feb. 21, 2013.
Notice of Allowance from U.S. Appl. No. 12/888,403, dated Nov. 22, 2013.
Non-Final Office Action from U.S. Appl. No. 12/888,403, dated Jun. 14, 2013.
Non-Final Office Action from U.S. Appl. No. 12/888,403, dated Sep. 20, 2012.
Advisory Action from U.S. Appl. No. 12/888,408, dated Feb. 26, 2015.
Final Office Action from U.S. Appl. No. 12/888,408, dated Dec. 10, 2014.
Non-Final Office Action from U.S. Appl. No. 12/888,408 dated May 23, 2014.
Examination Report from European Application No. GB1312478.9, dated Nov. 28, 2018.
Notice of Allowance from U.S. Appl. No. 14/869,734, dated Dec. 17, 2018.
Non-Final Office Action from U.S. Appl. No. 15/096,175, dated Dec. 27, 2018.
Notice of Allowance from U.S. Application No. 15/169,479, dated Jul. 12, 2018.
Restriction Requirement from U.S. Application No. 15/096,175, dated Jul. 27, 2018.
Supplemental Notice of Allowance from U.S. Application No. 15/169,479, dated Aug. 15, 2018.
Final Office Action from U.S. Application No. 14/869,734, dated Sep. 27, 2018.
Notice of Allowance from U.S. Application No. 14/869,734, dated Jan. 30, 2019.
Supplemental Notice of Allowance from U.S. Application No. 14/869,734, dated Mar. 20, 2019.
Corrected Notice of Allowance from U.S. Appl. No. 14/869,734, dated Apr. 30, 2019.

SAMPLE ASSEMBLY WITH AN ELECTROMAGNETIC FIELD TO ACCELERATE THE BONDING OF TARGET ANTIGENS AND NANOPARTICLES

CROSS-REFERENCES TO RELATED APPLICATIONS

The present application is related to coassigned U.S. patent application Ser. No. 12/888,388 entitled "DETECTION OF ANALYTES VIA NANOPARTICLE-LABELED SUBSTANCES WITH ELECTROMAGNETIC READ-WRITE HEADS", Ser. No. 12/888,394 entitled "READ-AFTER-WRITE DETECTION OF ANALYTES VIA NANOPARTICLE-LABELED SUBSTANCES", U.S. patent application Ser. No. 12/888,403 entitled "A SERVO CONTROL CIRCUIT FOR DETECTING ANALYTES VIA NANOPARTICLE-LABELED SUBSTANCES WITH ELECTROMAGNETIC READ-WRITE HEADS", and U.S. patent application Ser. No. 12/888,408 entitled "A CIRCUIT FOR DETECTING ANALYTES VIA NANO-PARTICLE-LABELED SUBSTANCES WITH ELECTROMAGNETIC READ-WRITE HEADS," all of which were filed on Sep. 22, 2010, and coassigned U.S. patent application Ser. No. 12/970,837 entitled "TRENCHED SAMPLE ASSEMBLY FOR DETECTION OF ANALYTES WITH ELECTROMAGNETIC READ-WRITE HEAD," which was filed on Dec. 16, 2010. The contents of the related applications are hereby incorporated by reference.

BACKGROUND

The present invention relates to analytical devices and processes, and more particularly, to devices and processes that incorporate electromagnetic write-heads and magneto-resistive read-sensors to detect target antigens.

It is known that antibodies bind with antigens as part of the human disease defense system. Presently, antigens are detected by such techniques as immunofluorescence, immunoperoxidase, or enzyme-linked immunosorbent assay (ELISA), each of which then employs a microscope for visual detection of the target antigen. It is desirable to exploit the use of magnetic signaling technology to automate the detection of analytes, such as antigens, and to further apply this technology to the detection of any biological matter.

SUMMARY

Described are embodiments of a sample assembly for detection of analytes with electromagnetic read heads.

In one embodiment, a sample assembly includes: a substrate; one or more base layers above the substrate; an outer layer above the substrate; a plurality of sample trenches formed in the outer layer, each sample trench being characterized by an upper surface, a bottom surface, and a longitudinal axis; an electrical conductor disposed in the substrate, the electrical conductor being configured to generate an electromagnetic field in proximity to the plurality of sample trenches to enhance nanoparticle movement toward the bottom surface of the plurality of sample trenches; and at least one alignment trench formed above the substrate, each alignment trench having a longitudinal axis substantially parallel to a longitudinal axis of at least one of the sample trenches.

In another embodiment, a method of forming a sample assembly of a biological sample having target antigens includes: providing a substrate having a surface and an embedded electrical conductor; bonding a first set of antibodies on the substrate surface; exposing the substrate surface with the first set of bonded antibodies to the biological sample having the target antigens, where the target antigens bond with the first set of antibodies on a bottom surface of each of a plurality of sample trenches, each sample trench having a substantially linear shape and being formed in an outer layer disposed above the substrate, at least some of the sample trenches being in proximity to one or more alignment trenches having a longitudinal axis substantially parallel to a longitudinal axis of the proximate sample trench, and each alignment trench comprising markings configured to facilitate alignment of an electromagnetic write head of a magnetic tape drive. The method also includes: bonding a second set of antibodies to nanoparticles, where the first and second sets of antibodies are biologically identical; exposing the target antigens bonded with the first set of antibodies to the second set of antibodies bonded with the nanoparticles, wherein the second set of antibodies bond with the target antigens; and applying an electric current through the electrical conductor to generate an electromagnetic field, where the electromagnetic field generated by applying the electric current through the electrical conductor comprises an electrical component and a magnetic component, where the magnetic component of the electromagnetic field moves the nanoparticles toward the bottom surface of the plurality of sample trenches, and where moving the nanoparticles toward the bottom surface of the plurality of sample trenches speeds up the bonding between the second set of antibodies and the target antigens.

In yet another embodiment, a method of detecting target antigens in a biological sample on a sample assembly including a substrate having a surface and an electrical conductor includes the following steps: bonding a first set of antibodies on the substrate surface exposed via one or more sample trenches formed in an outer layer positioned above the substrate surface, each sample trench having a longitudinal axis and a substantially linear shape arranged along the longitudinal axis thereof, at least one of the sample trenches being in proximity to one or more alignment trenches having a longitudinal axis substantially parallel to the longitudinal axis of the proximate sample trench, and each alignment trench comprising markings configured to facilitate alignment of an electromagnetic write head of a magnetic tape drive; exposing the substrate surface with the first set of bonded antibodies to the biological sample having the target antigens, where the target antigens bond with the first set of antibodies; bonding a second set of antibodies to nanoparticles, where the first and second sets of antibodies are biologically identical; exposing the target antigens bonded with the first set of antibodies to the second set of antibodies bonded with the nanoparticles, where the second set of antibodies bond with the target antigens; applying an electric current through the electrical conductor to generate an electromagnetic field, where the electromagnetic field generated by applying the electric current through the electrical conductor comprises an electrical component and a magnetic component, where the magnetic component of the electromagnetic field moves the nanoparticles toward bottom surface of the one or more sample trenches, and where the moving the nanoparticles toward the bottom surface of the one or more sample trenches speeds up the bonding between the second set of antibodies and the target antigens; magnetizing the nanoparticles using an electromagnetic write head; and reading the magnetized nanoparticles using a magneto-resistive read sensor to detect the target antigens.

For a fuller understanding of the present invention, reference should be made to the following detailed description taken in conjunction with the accompanying drawings.

DETAILED DESCRIPTION OF THE INVENTION

The invention is described in exemplary embodiments with reference to the Figures, in which like numbers represent the same or similar elements. It will be appreciated by those skilled in the art that variations may be accomplished in view of these teachings without deviating from the spirit or scope of the invention.

Exemplary embodiments of the invention relate to a sample assembly for detection of analytes with electromagnetic read heads. The substrate of the sample assembly includes an electrical conductor for generating an electromagnetic field that accelerates the bonding between target antigens in the analytes and nanoparticle-labeled antibodies. In one embodiment, the sample substrate includes a sample trench that has a first set of antibodies bonded on the bottom surface of the sample trench. The first set of antibodies are bonded to the target antigens.

Further, nanoparticles are bonded to a second set of antibodies which are then exposed to the sample trench so that the second set of antibodies are bonded with the target antigens. To speed up the bonding between nanoparticle-labeled antibodies and the target antigens, an electrical conductor embedded in or attached to the sample substrate generates an electromagnetic field that moves the nanoparticle-labeled antibodies toward the target antigens attached to the bottom of a sample trench or on the surface of a sample substrate.

A head module includes a write head for magnetizing nanoparticles and a magneto-resistive read sensor for detecting the magnetized nanoparticles, and thus, the target antigens. The sample trench constrains the biological sample, and thus the target antigens, during the preparation and subsequent analysis of the biological sample. Accordingly, the target antigens are aligned with read elements of a head module such that the target antigens are reliably and accurately detected. Further, to ensure reliable and accurate detection, an outer layer may be formed with a low friction material allowing the read head to remain in contact with the upper surface of the outer layer during the process of detection.

Figure 1:
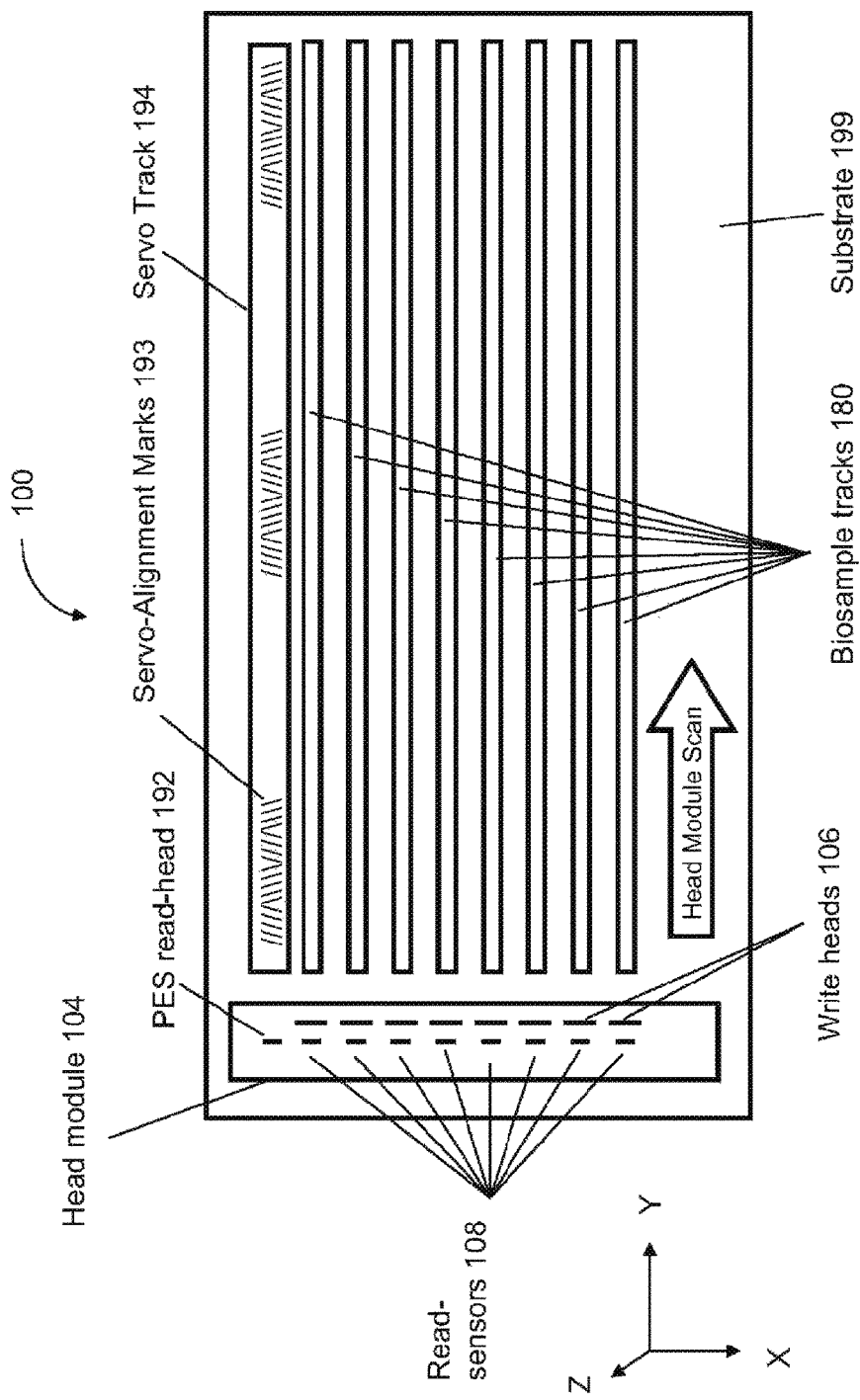
FIG. 1 is a top view of a sample assembly in accordance with an embodiment of the invention.

FIG. 1 is a top view of a sample assembly 100, not drawn to scale, in accordance with an embodiment of the invention. The sample assembly 100 includes a substrate 199. The substrate 199 may comprise, without limitations, a Peltier hard-substrate, a glass substrate, a polyethylene terephthalate (PET, which is commonly known by the trade name of Mylar® substrate, a flexible-substrate, or other materials having similar properties. The term "substrate" refers to any supporting structure, including, but not limited to, the substrates described above. Further, the substrate may include of more than one layer of material.

In one embodiment, the substrate 199 may have an outer layer 253 (FIG. 2) that comprises diamond-like-carbon (DLC), polytetrafluoroethylene, aluminum oxide, polyamides, or other low-friction materials known in the art. Deposition techniques utilized herein include, but are not limited to, photolithography, silk-screening, and other similar processes. The outer layer 253 may be formed to a thickness of between 0.2 to 60 microns. The outer layer 253 includes sample trenches (or sample tracks) 180. The process of forming the sample trenches 180 is described with respect to FIGS. 2A and 2B.

Figure 2A:
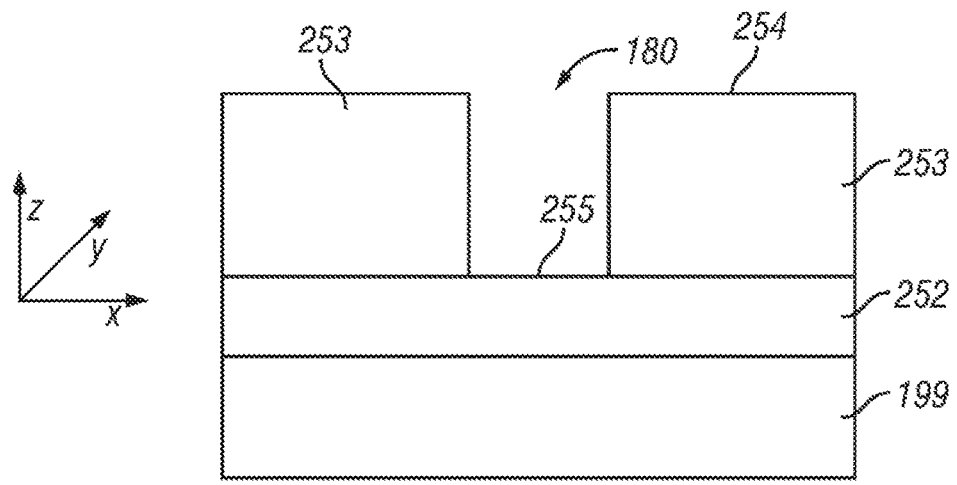
FIG. 2A is a cross-sectional view of a portion of a sample assembly including a sample trench in accordance with an embodiment of the invention.

One embodiment of forming sample trenches 180 is illustrated in FIG. 2A. In this embodiment, a base layer 252 is formed on substrate 199. Base layer 252 may comprise nonmagnetic materials such as gold, silicon, or $SiO_2$, or other materials having similar magnetic properties, without limitation. An outer layer 253 is then formed on base layer 252. Outer layer 253 has an upper surface 254. A plurality of sample trenches 180 are formed within outer layer 253. Sample trenches 180 may be formed by known methods in the art including laser milling, x-ray milling, or photolithographically. Sample trenches 180 may be formed to have a depth of between 0.2 to 60 microns. It should be understood by one of ordinary skill in the art that, while only one sample trench is shown, a plurality of sample trenches 180 may be formed within the outer layer 253 with the same method described herein. Each sample trench 180 is formed having a bottom surface 255. In one embodiment, the bottom surface of the trench exposes base layer 252.

Figure 2B:
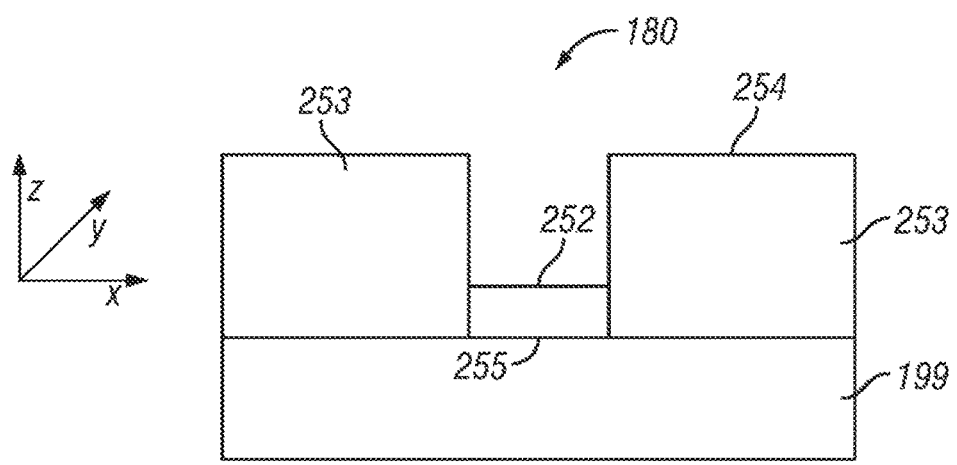
FIG. 2B is a cross-sectional view of a portion of a sample assembly including a sample trench in accordance with another embodiment of the invention.

Another embodiment of forming sample trenches 180 is described with respect to FIG. 2B. In this embodiment, outer layer 253 is formed on substrate 199. The outer layer 253 has an upper surface 254. A plurality of sample trenches 180 are formed within outer layer 253. Sample trenches 180 may be formed by known methods in the art including laser milling, x-ray milling, or photolithographically. Sample trenches may be formed to have a depth of between 0.2 to 60 microns. It should be understood by one of ordinary skill in the art that, while only one sample trench is shown, a plurality of sample trenches 180 may be formed within the outer layer 253 with the same methods described herein.

Each sample trench 180 is formed having a bottom surface 255. Base layer 252 is formed within each sample trench 180 and on the bottom surface 255 of each sample trench 180. Base layer 252 may comprise nonmagnetic materials such as gold, silicon, or $SiO_2$, or other materials having similar magnetic properties, without limitations. As shown in FIG. 2B, the base layer 252 only partially fills sample trenches 180. There are many embodiments in which base layer 252 may be formed to only partially fill sample trenches 180. For example, in one embodiment, base layer 252 may be formed conformally over the outer layer 253 and within sample trenches 180. Base layer may then be removed by etching or planarization techniques known in the art. Alternatively, the base layer 252 may be selectively deposited by known methods in the art. The described embodiment of forming a base layer 252 only within the sample trench 180 is particularly advantageous in embodiments in which expensive materials are utilized, such as gold since much less material is required to form the base layer 252.

As shown in FIG. 1, eight sample trenches 180 may be formed to correspond to the head module 104 of the IBM® TS 1130 tape drive writing with eight write elements 106 and reading with eight read sensors 108 simultaneously, as further explained below. The sample trenches 180 are parallel to each other and extend along the Y-axis.

Figure 2C:
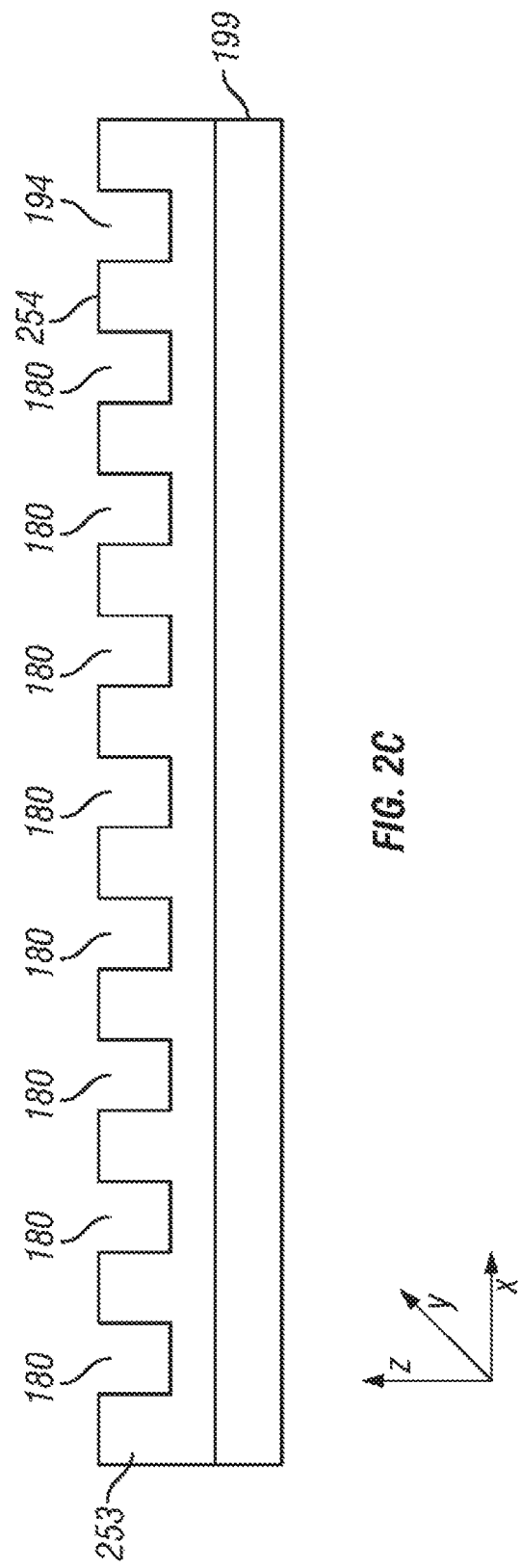
FIG. 2C is a cross-sectional view of sample assembly including sample trenches and an alignment trench in accordance with an embodiment of the invention.

In one embodiment, as shown in FIGS. 1 and 2C, the outer layer 253 further includes at least one servo alignment track 194 with a plurality of magnetic servo alignment marks 193. The servo alignment track 194 is parallel with the sample trenches 180 and extends along the Y-axis. The servo alignment track 194 may be a servo alignment trench 194 with a plurality of magnetic servo alignment marks 193. FIG. 2C shows a cross section of substrate 199 along the X-axis illustrating an embodiment in which an alignment trench 194 is formed within outer layer 253. For simplicity of illustration, base layer 252 is not illustrated in FIG. 2C. Alignment trench 194 may be formed in the same manner as described for forming sample trenches 180 shown in FIGS. 2A and 2B. In one embodiment, alignment trench 194 is formed simultaneously with the formation of sample trenches 180. Specifically, alignment trench 194 may be formed by known methods in the art including laser milling, x-ray milling, or photo-lithography. Alignment trench 194 may have a depth of between 0.2 to 60 microns. It should be understood by one of ordinary skill in the art that, while only one alignment trench 194 is shown, a plurality of alignment trenches 194 may be formed within the outer layer 253 as described herein. For example, alignment trenches 194 could be formed between each of the sample trenches 180.

In another embodiment, magnetic encoded servo alignment marks 193 are encoded on a piece of magnetic tape which is adhered to outer layer 253. Further, the magnetic encoded servo alignment marks 193 may be encoded by the manufacturer of substrate 199 on the magnetic tape. Magnetic encoded servo alignment marks 193 may be in the form of timing based servo marks. Servo alignment marks 193 are read by read sensor 106 and used to keep the write elements 108 and read sensors 106 in alignment with sample trenches 180 along the X-axis while the head module 104 moves relative to sample trenches 180 along the Y-axis.

Still further, in one embodiment the alignment marks 193 may be non-magnetic marks. For example, the alignment marks may be lithographed, silk-screened or ink-jet printed, and read with an optical laser.

The sample trenches 180 include a biological sample having a target antigen. Sample trenches 180 act to constrain the biological sample, and thus the target antigen 210, during the preparation and subsequent analysis of the biological sample, as discussed below. For example, the sample trenches 180 prevent the biological sample from being rinsed away during a rinse step. Further, the sample trenches 180 allow the biological sample and the target antigen to be constrained to an area that is aligned with read elements 108, such that detection of target antigen 210 is reliably and accurately detected.

Figure 3:
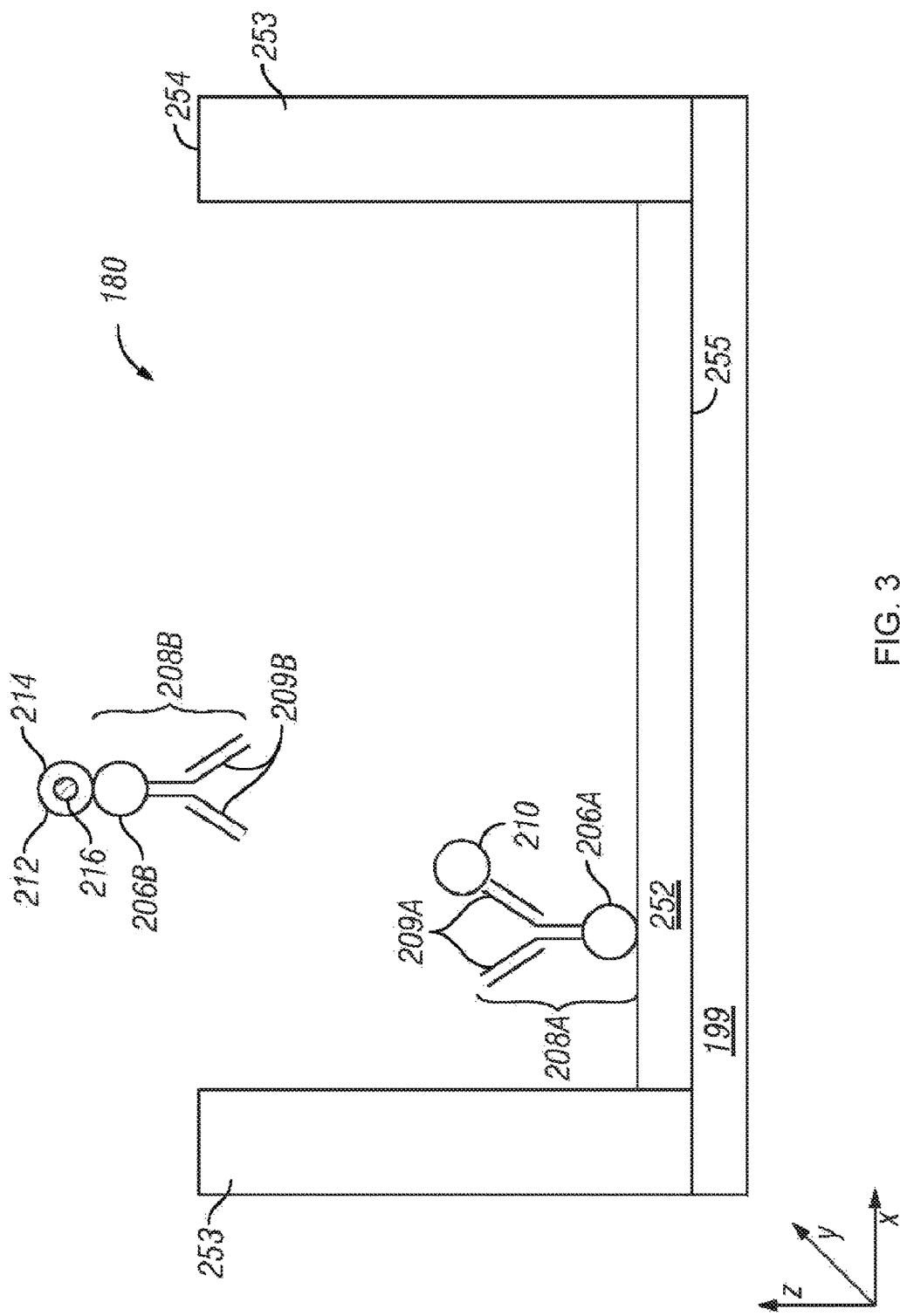
FIG. 3 is a cross-sectional view of a sample trench that includes a biological sample with target antigens that are bonded with antibodies attached to the bottom of a sample trench, before the target antigens are bonded with nanoparticle-labeled antibodies, in accordance with an embodiment of the invention.
Figure 4:
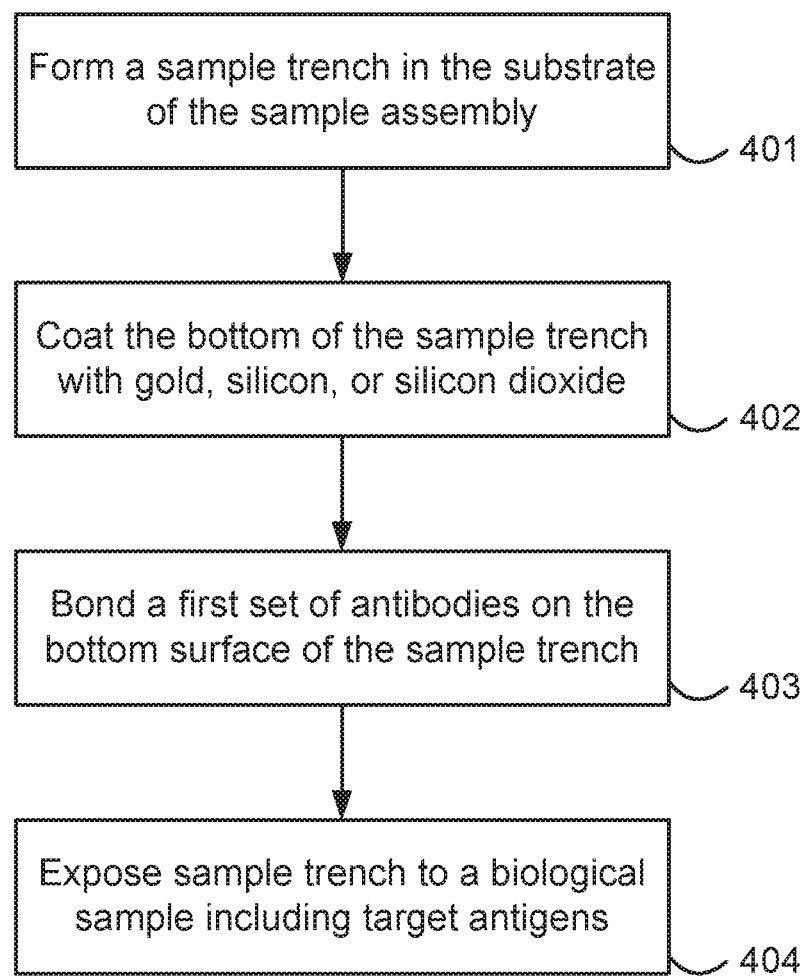
FIG. 4 is a flow chart illustrating example steps for preparing sample assembly with target antigens for an analytic process in accordance with an embodiment of the invention.

The preparation of the biological sample with target antigens 210 is now discussed with reference to FIGS. 3 and 4. FIG. 3 shows an example sample trench 180 that has an antibody 208A and a target antigen 210 bonded to the bottom surface of the sample trench 180. The sample trench 180 may be formed in the base layer 252 by any of the methods described herein. Further, an outer layer 253 and multiple sample trenches 180 may be formed, as discussed above. FIG. 4 shows an example process for preparing and bonding target antigen 210 to the sample trench 180. At step 401, at least one sample trench 180 is formed in the sample assembly 100. The sample trench 180 may be formed in the outer layer 253 of the sample assembly 100.

In step 402, a base layer 252 may be formed on the bottom surface 255 of the sample trench 180 by coating the bottom surface 255 with gold, silicon, or silicon dioxide to facilitate attaching antibodies to the sample trench 180. In step 403, antibodies 208A are bonded within sample trenches 180 to the surface of base layer 252. The antibodies 208A may be bonded within the sample trenches to the base layer 252 via bonds 206A such as amide, self-assembled-monolayers (SAMS), alkoxysilane, organic functional trialkoxysilane, thiol bonds, or the like.

In one embodiment, it is preferred that bond 206A is applied only to the surface of base layer 252. In one example, the bonding comprises coating base layer 252 with amide, self-assembled-monolayers (SAMS), alkoxysilane, or thiol, placing a solution of antibodies 208A on substrate 199, and gently rocking substrate 199 for a period of time, up to six hours. Amide refers to organic compounds that include the functional group including an acyl group, with the chemical notation C=O, linked to a nitrogen (N) atom. A SAM is an organized layer of amphiphilic molecules in which one end of the molecule, the "head group," shows a special affinity for gold, silicon, or $SiO_2$, such as that utilized in base layer 252. At the terminal end, the opposite end of the SAM from the "head group" is a functional group. In one embodiment, the first set of antibodies 208A are attached to this functional group in step 403. Lastly, a thiol is a compound that includes the functional group composed of a sulfur atom and a hydrogen atom (—SH). Being the sulfur analog of an alcohol group (—OH), this functional group is referred to either as a thiol group or a mercaptan group.

There are generally five known isotopes (types) of antibodies 208A and 208B for mammals. In FIG. 3, the Y-shape of antibodies 208A and 208B are that of monomer antibodies. There are three isotopes of monomer antibodies: IgD, IgE, and IgG, where the prefix Ig is the symbol for Immunoglobulin, and these monomer antibodies each have one unit of Ig. There is only one isotope of a dimer antibody, IgA, which has two Ig units. Finally, there is only one isotope of pentamer antibody, IgM, which has five Ig units. These antibodies are further described in copending and coassigned U.S. patent application Ser. No. 12/888,388 entitled "DETECTION OF ANALYTES VIA NANOPARTICLE-LABELED SUBSTANCES WITH ELECTROMAGNETIC READ-WRITE HEADS", which is incorporated herein by reference. The analytical process described herein may be used in human medicine, veterinarian medicine, and, as well as to other biological analyses.

In one embodiment, step 403 may include rinsing substrate 199 with water or another rinsing agent to remove any antibodies 208A that are not bonded within sample trenches 180. In all rinsing steps discussed herein a surfactant may be added to the water or rinsing agent to reduce surface tension. In one example, the surfactant may include a detergent solution.

In step 404, antibodies 208A bonded within sample trench 180 are exposed to a biological sample including target antigens 210. In one example, this is accomplished by placing a blood sample or other biological sample on substrate 199. As shown in FIG. 3, the target antigens 210 bond to monomer antibodies 208A at antigen receptors 209A. The antigen receptors 209A are diagrammatically shown to be at the v-shaped end of antibodies 208A. As shown, each monomer antibody 208A has two antigen receptors 209A. Step 404 may include the repetitive rocking of substrate 199 to facilitate bonding of the target antigens 210 with antibodies 208A at antigen receptors 209A. For example the substrate is gently rocked for up to six hours. Further, step 404 may include a step of rinsing substrate 199 with water or another rinsing agent to remove antigens 210 not bonded to antibodies 208A.

Target antigens 210 may comprise cancer cells, viruses, or bacteria. In one embodiment, the target antigens 210 are viruses such as Human Papilloma Virus (HPV) which is known to lead to cancer. It is important to note that the antibodies 208A utilized in step 404 are specifically chosen based on the targeted antigens 210 utilized in step 406.

Figure 5:
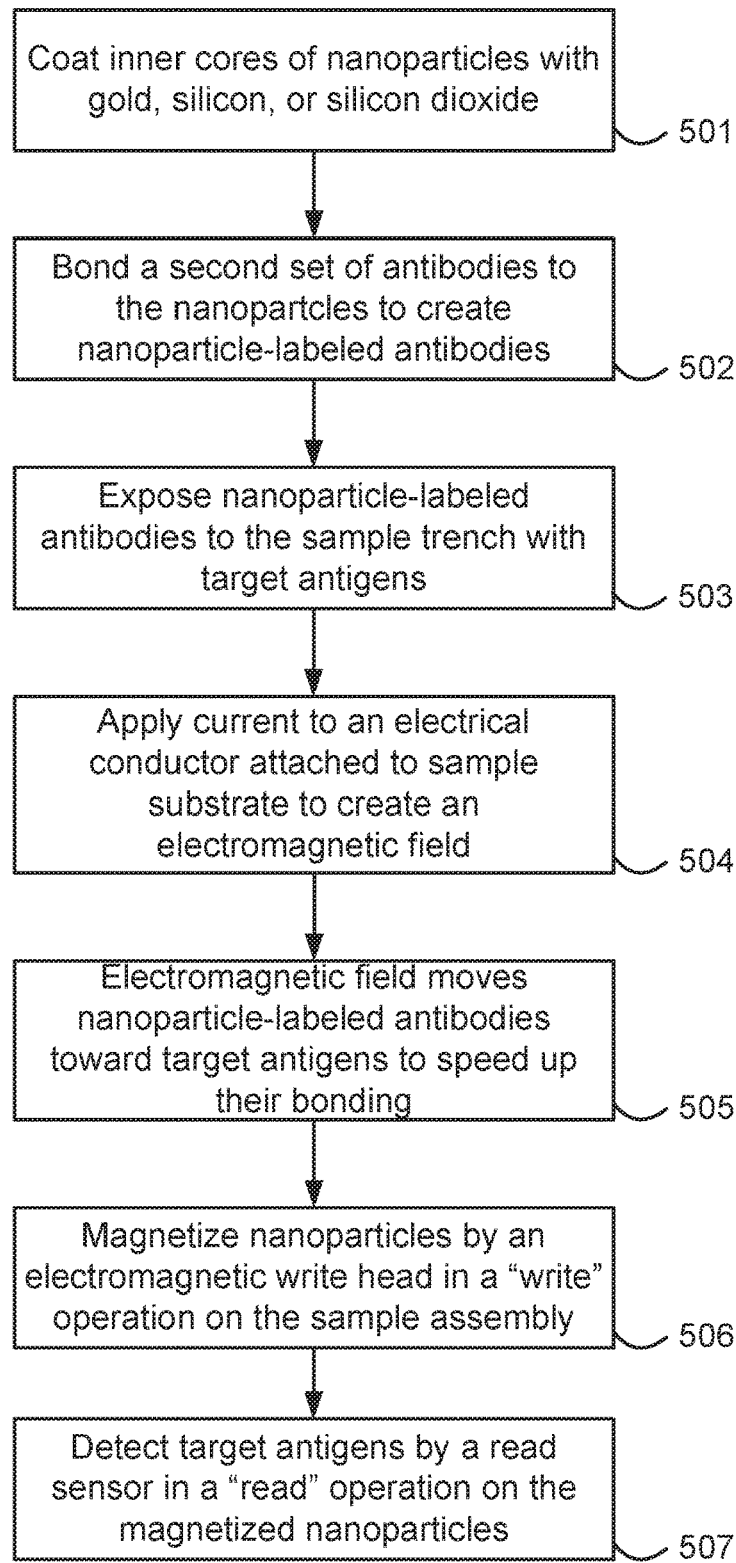
FIG. 5 is a flow chart illustrating example steps for preparing nanoparticle-labeled antibodies to be bonded to target antigens, magnetizing the nanoparticles, and detecting the target antigens in an analytic process in accordance with an embodiment of the invention.

FIG. 5 is a flow chart of an example process for preparing nanoparticle-labeled antibodies 208B, facilitating the bonding of the nanoparticle-labeled antibodies 208B to target antigens 210, and detecting the target antigens 210 in a biological sample. Nanoparticles 212 may include a magnetic inner core 216 and an outer shell 214. Magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality.

In one embodiment, the nanoparticles 212 may be prepared prior to bonding the nanoparticles 212 to antibodies 208B, via bonds 206B, to prevent a lumping of the nanoparticles 212 when they are magnetized. This preparation may include demagnetizing the magnetic inner cores 216, as described in the pending U.S. patent application Ser. No. 12/970,831, the content of which is herein incorporated by reference. In one embodiment, inner cores 216 are initially nonmagnetized as an artifact of their manufacturing process. In an alternate embodiment, inner cores 216 are not demagnetized.

The process in FIG. 5 may begin at step 501 in which the inner cores 216 are coated with gold, silicon, or silicon dioxide to create nanoparticles 212. In step 502, the second set of antibodies 208B are bonded with nanoparticles 212 via bonds 206B. It is important to note that the first set of antibodies 208A and the second set of antibodies 208B are biologically identical, as both bond to the same target antigen 210. In one embodiment, the second set of antibodies 208B are bonded with nanoparticles 212 via bonds 206B in parallel with steps 402 and 403. In other embodiments, the second set of antibodies 208B may be bonded with nanoparticles 212 before or after steps 402 and 403.

The second antibodies 208B may be bonded to the nanoparticles 212 via amide, self-assembled-monolayers (SAMS), alkoxysilane, organic functional trialkoxysilane, or thiol bonds 206B. This bonding may be accomplished by first coating nanoparticles 212 with amide, self-assembled-monolayers (SAMS), alkoxysilane, organic functional trialkoxysilane, or thiol. It is important to note that the material used for the outer shell 214 facilitates the bonding of antibody 208B within sample trench 180. The nanoparticles 212 may be placed in a solution including the second set of antibodies 208B and gently rocking this solution for a period of time. The repetitive rocking of substrate 199 facilitates bonding of the second set of antibodies 208B with the nanoparticles 212. For example, the substrate is gently rocked for up to six hours. Further, step 502 may include a step of rinsing the sample substrate 199 with water or another rinsing agent to remove nanoparticles 212 not bonded to antibodies 208B.

In step 503, the biological sample with the target antigens 210 is exposed to the second set of antibodies 208B bonded to nanoparticles 212. This may be done by placing a solution of nanoparticle-labeled antibodies 208B on substrate 199, such as in sample trench 180. As shown in FIG. 3, the target antigens 210 bond with the antigen receptors 209B of antibodies 208B. In step 504, electrical current is applied to the conductor, to create an electromagnetic B field, and in step 505, the gradient of this electromagnetic B field draws the nanoparticle-labeled antibodies 208B towards substrate 199 so that antigens 210 may identified. Steps 504 and 505 may include using an exterior auxiliary permanent magnet, or an electromagnet not physically coupled to sample assembly 100, such as magnet 804 in FIG. 8, to strengthen the applied electromagnetic B field.

Steps 504 and 505 may further include the repetitive rocking of substrate 199 to facilitate bonding of the target antigens 210 with antibodies 208B at antigen receptors 209B. For example, the substrate is gently rocked for up to six hours. Step 505 may include the use of an exterior auxiliary permanent magnet or an electromagnet not physically coupled to sample assembly 100 to strengthen the applied electromagnetic B field. Further, step 505 may include a step of rinsing substrate 199 with water or another rinsing agent to remove nanoparticles 212 not bonded to target antigens 210. At the conclusion of steps 504-505, the current in the conductor may be turned off so that the electromagnetic B field does not interfere with magnetizing step 506 or sensing step 507. Similarly, if auxiliary magnet 804 is used in steps 504-505, that magnet 804 may be removed at this time as well so that it does not interfere with magnetizing step 506 or sensing step 507.

Figure 6:
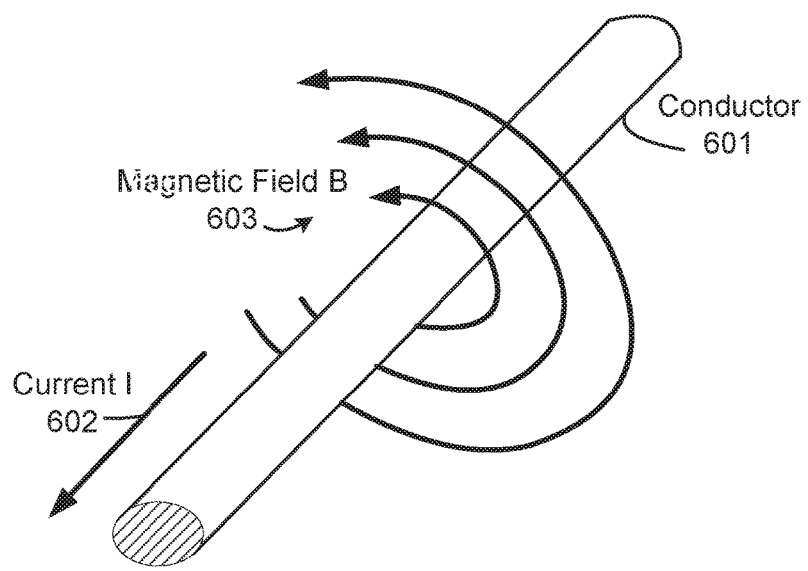
FIG. 6 illustrates an electromagnetic field generated by an electric current flowing through an electrical conductor.

In one embodiment, the substrate 199 includes an electrical conductor 601 for generating an electromagnetic field that moves the nanoparticle-labeled antibodies 208B towards the bottom of the sample trench 180 to speed up the bonding of the antibodies 208B and the target antigens 210. As illustrated in FIG. 6, when an electric current I (602) flows through the electrical conductor 601, it generates an electromagnetic field B (603) according to Ampere's circuital law. The direction of the electromagnetic filed B (603) is indicated in FIG. 6 according to the "right-hand" rule in which one's right-hand thumb points in the direction of the electric current I (602) and one's fingers point in the direction of the resulting electromagnetic field B (603).

Figure 7:
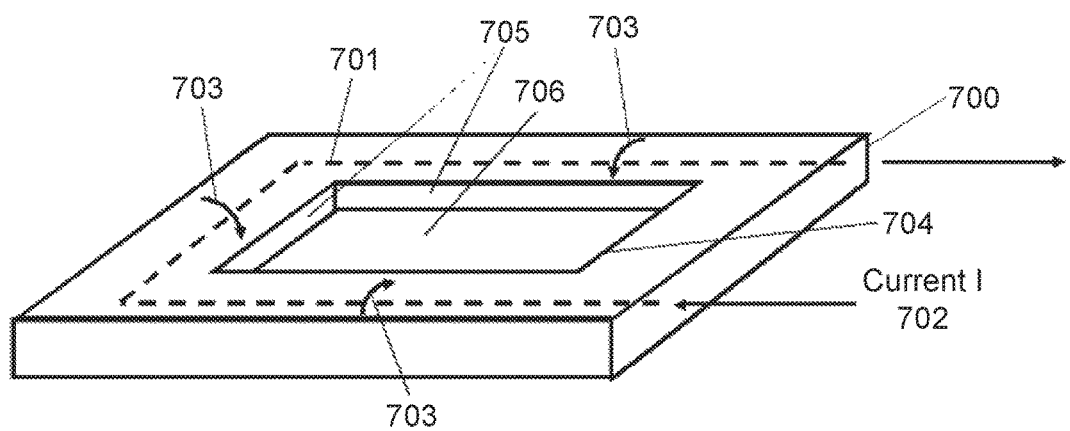
FIG. 7 illustrates an electrical conductor embedded in the substrate of a sample assembly to generate an electromagnetic field to speed up the bonding between target antigens and nanoparticle-labeled antibodies, in accordance with an embodiment of the invention.

FIG. 7 illustrates an example embodiment in which the substrate 700 of a sample assembly includes an embedded electrical conductor 701 for generating an electromagnetic B field 703 when an electric current I (702) passes through the electrical conductor 701. The substrate 700 includes a sample trench 704 having trench walls 705. In one embodiment, the electrical conductor 701 may be embedded in the substrate 700 along the walls 705 of the sample trench 704 and below plane of the bottom surface 706 of the sample trench 704. The electromagnetic field 703 acts on the nanoparticles 212 and pulls the nanoparticle-labeled antibodies 208B in the sample trench 704 toward the bottom surface 706 to which the target antigens 210 and antibodies 208A are attached (not shown). This movement speeds up the bonding between the nanoparticle-labeled antibodies 208B and the target antigens 210, which would otherwise take place at a slower pace when the nanoparticle-labeled antibodies 208B descend to the bottom surface 706 by gravity alone.

It is preferred that the electrical conductor 701 is positioned below the plane of the bottom surface 706 so that the gradient of the electromagnetic field B (703) continues to increase as the nanoparticle-labeled antibodies 208B descend to the bottom surface 706. Empirical data indicate that the movement of the nanoparticle-labeled antibodies 208B toward the bottom surface 706 is increased by nearly two orders of magnitude times faster than their movement by gravity alone, with the nanoparticles 212 moving in water and an electric current I (702) of one ampere.

Figure 8:
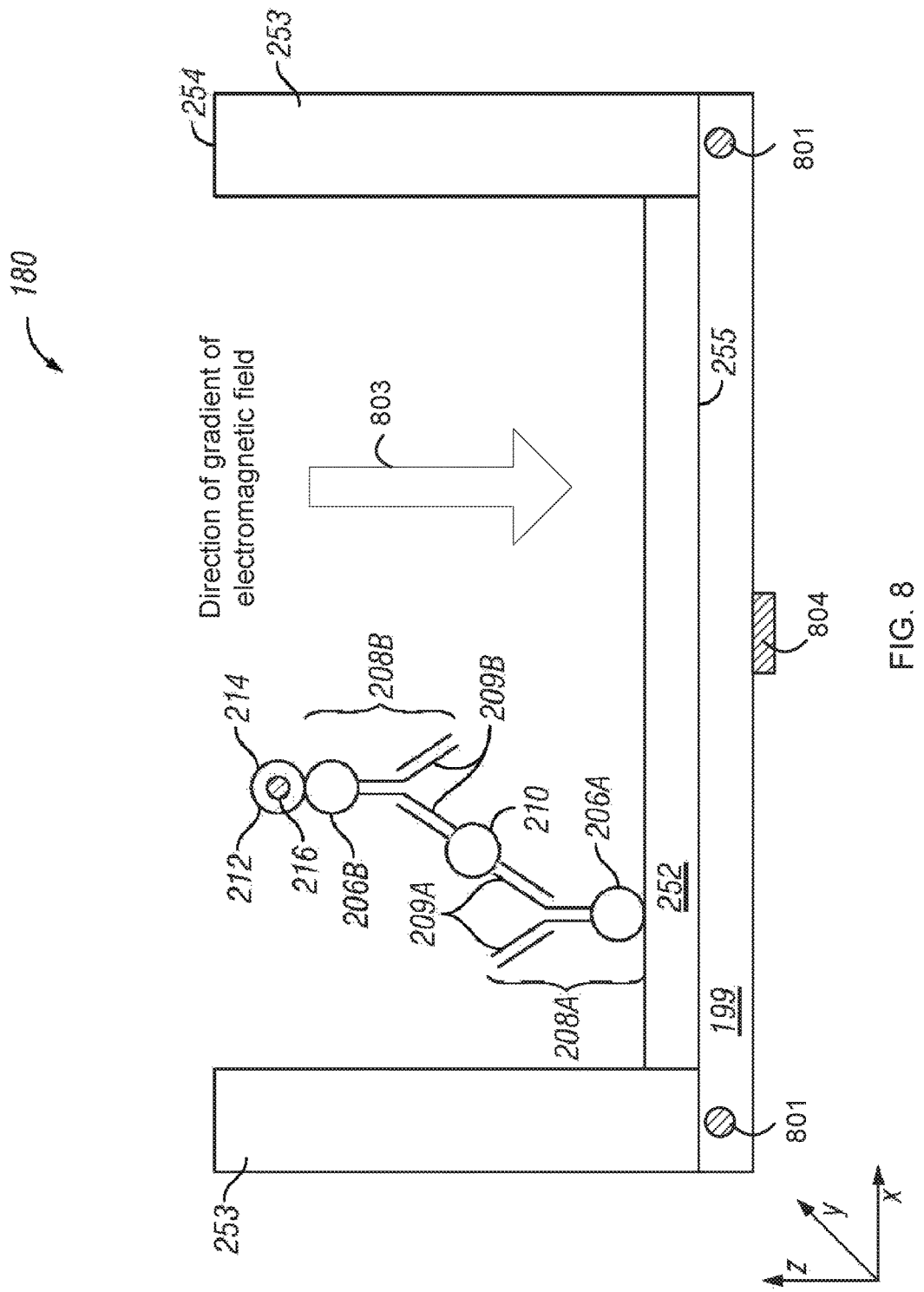
FIG. 8 illustrates the effect of an electromagnetic field in moving the nanoparticle-labeled antibodies toward the bottom of a sample trench to speed up the boding between the nanoparticle-labeled antibodies and target antigens, in accordance with an embodiment of the invention.

FIG. 8 is a cross sectional view of a sample trench 180 that illustrates the effect of the gradient of electromagnetic field) B (703) in moving a nanoparticle-labeled antibody 208B toward the bottom of the sample trench 180 to speed up the bonding between the nanoparticle-labeled antibody 208B and target antigen 210. As an example, electrical conductor 801 is embedded in the substrate 199 and below the plane of the bottom surface 255 of the sample trench 180. Arrow 803 indicates the direction of the increasing gradient of electromagnetic field B (703) which moves the nanoparticle-labeled antibody 208B toward the target antigens 210 to accelerate their bonding process. An exterior auxiliary permanent magnet 804 or an electromagnet not physically coupled to sample assembly 100 may be used to strengthen the applied electromagnetic B field (703).

Figure 9:
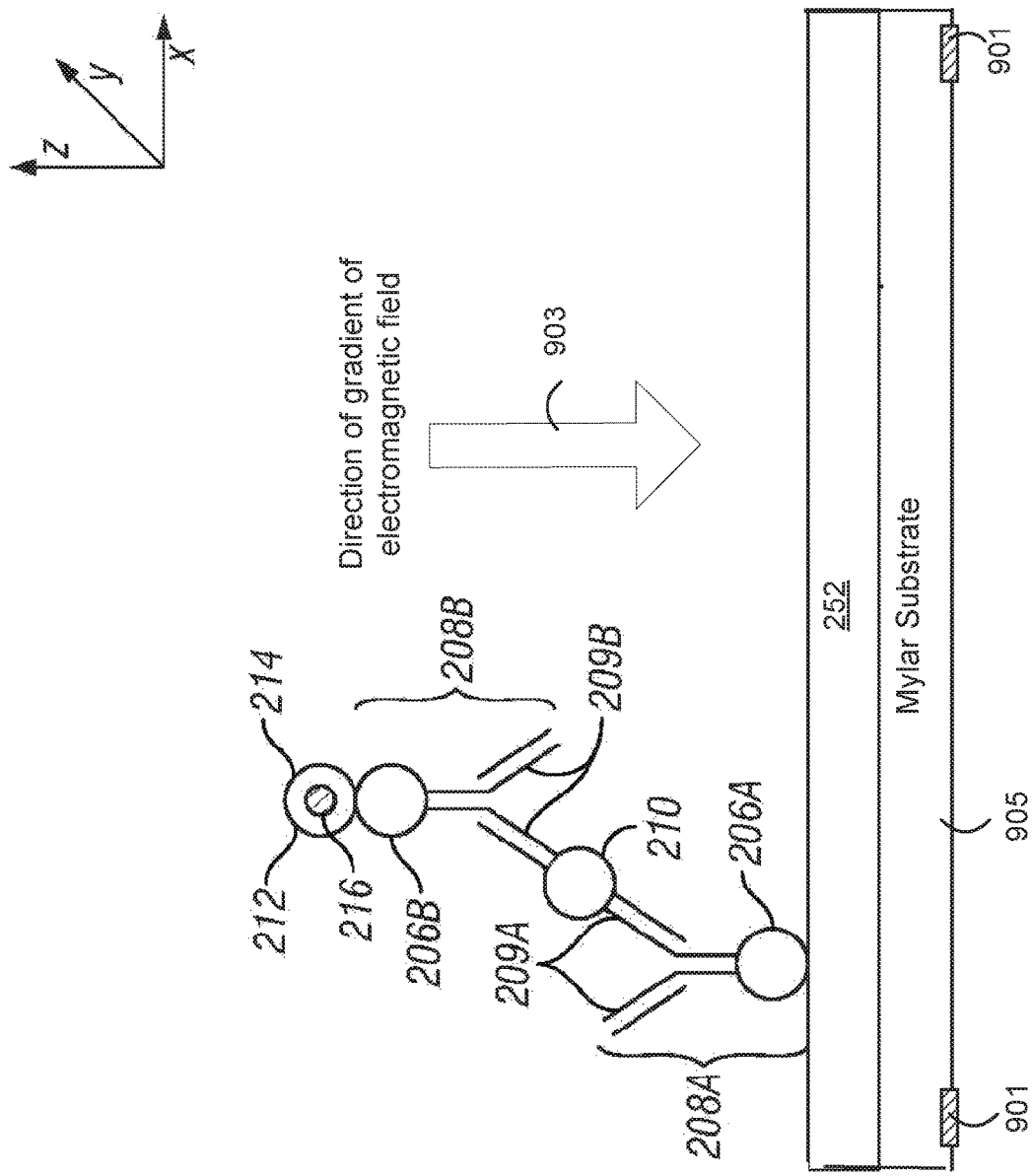
FIG. 9 illustrates the effect of an electromagnetic field in moving the nanoparticle-labeled antibodies toward a Mylar® film substrate to speed up the boding between the nanoparticle-labeled antibodies and target antigens, in accordance with an embodiment of the invention.

FIG. 9 is a cross sectional view of a sample substrate 199 in the form of a Mylar® film that illustrates the effect of the increasing gradient of electromagnetic field B (903) in moving the nanoparticle-labeled antibodies 208B toward the Mylar® film substrate 199 to speed up the boding between the nanoparticle-labeled antibodies 208B and target antigens 210. As an example, an electrically conducting metal trace 901, e.g., a copper trace, may be attached to bottom surface 905 of the Mylar® substrate 199 as illustrated in FIG. 9. In one embodiment, metal trace 901 is a thin film deposition of a conductor, such as copper, gold, aluminum, silver, and the like. When an electric current I (602) goes through the electrical trace 901, it generates an electromagnetic field B (603) which moves the nanoparticle-labeled antibodies 208B toward the target antigens 210 the accelerate their bonding process. Arrow 903 indicates the direction of the increasing gradient of electromagnetic field B (603).

In the embodiment in which substrate 199 is a Peltier substrate, the process may include an optional step of applying a DC voltage of a first polarity to the Peltier substrate. Applying a DC voltage of a first polarity heats the surface of the substrate 199 and dries the biological sample within the sample trench 180. A DC voltage of a second and opposite polarity may be applied to Peltier substrate, to cool the surface of the substrate. In an alternate embodiment, the Peltier substrate freezes the biological sample.

Returning to FIG. 1, head module 104 includes electromagnetic write-heads 106 and magneto-resistive read-sensors 108 arranged in pairs, such that each write head 106 is paired with a read sensor 108. The write head 106 may be a thin film write element. The electromagnetic write-heads 106 first write to sample trenches 180, and then the adjacent magneto-resistive read-sensors 106 immediately reads from sample trenches 180, which is referred to as a read-after-write operation. In an exemplary embodiment of the invention, the sample assembly 100 has eight sample trenches 180 corresponding to eight bits in a byte. Accordingly, in this embodiment, the head module includes eight electromagnetic write-head 106 and magnetoresistive read-sensor 108 pairs. Advantageously, this is the same number of write heads and read sensors in a typical head module used in magnetic tape drive products, such as IBM® TS 1130 tape drive. Therefore, in one embodiment, the head module 104 may be an IBM® TS 1130 head module. In another embodiment, the head module 104 may be an IBM® TS 1140 head module.

It should be understood, however, any number of sample trenches 180 may be used, and the number of electromagnetic write-head 106 and magneto-resistive read-sensor 108 pairs in head module 104 may be any number. The number may be in the range from one to the number of electromagnetic write-head and magneto-resistive read-sensor pairs the head module 104. For example, in an embodiment in which there are sixteen such electromagnetic write-head and magneto-resistive read-sensor pairs, such as in a head module of an IBM® 3480 tape drive, the number of sample trenches may be sixteen. In one embodiment, the number of sample trenches 180 is an integral multiple of the number of write-head 106 and read-sensor 108 pairs. Still further, in one embodiment, the write-head 106 and the read-sensor are not separate devices. Instead a single head may perform the functions of both the write-head 106 and read-sensor 108.

As mentioned above, the sample trenches 180 may have spacing from one sample trench to the adjacent sample trench along the X-axis to match the spacing from one read sensor 108 to the adjacent read sensor 108 along the X-axis. In one embodiment the spacing between one sample trench 180 and an adjacent sample trench 180 is 166.5 microns to match the read sensor to read sensor spacing of the IBM® TS1130 tape drive.

Write-heads 106 may be any write head known in the art. In one embodiment write-heads 106 comprise miniature electromagnets, with a coil sandwiched between two poles. Read-sensors 108 may be anisotropic magneto-resistive (AMR), giant magneto-resistive (GMR), or tunnel magnetoresistive (TMR) read-sensors, or other devices with similar functionality known in the art. GMR read-sensors, which are also known as spin-valve read-sensors, typically have an internal anti-parallel pinned layer for increased sensitivity. TMR read-sensors may utilize a tunnel barrier layer to augment the GMR internal structure and to provide increased sensitivity.

As shown in FIG. 1, write-head 106 may be longer along the X-axis direction than read-sensor 108. Accordingly, the active sensing portion of read-sensor 108 is smaller than write-head 106 along the X-axis. Write-head 106 is used to magnetize nanoparticle 212 for detection by read-sensor 108 as discussed below. It is advantageous for write-head to be longer in the X-direction than read-sensor 108 because it prevents read-sensor from encountering unmagnetized nanoparticles 212, and thus, registering a false-negative detection of target antigen 210.

Head module 104 is kept in linear alignment with sample trenches 180 along the X-axis by position-error-servo (PES) read-head 192, which reads magnetically encoded servo-alignment marks 193 from servo track 194 on sample assembly 100. PES read-head 192 may be, for example, an AMR, GMR, or TMR read-sensor. In the example illustrated in FIG. 1, servo-alignment marks 193 shown are Timing Based Servo (TBS) servo-alignment marks such as those used in IBM® Linear Tape Open (LTO) tape drive products and IBM® enterprise tape product models TS1120, TS1130, and TS1140. U.S. Pat. No. 6,320,719, entitled "Timing Based Servo System for Magnetic Tape Systems," is hereby incorporated by reference in its entirety for its showing of Timing Based Servo control and TBS servo-alignment marks. U.S. Pat. No. 6,282,051, entitled "Timing Based Servo System for Magnetic Tape Systems," is hereby incorporated by reference in its entirety for showing the writing of TBS servo-alignment marks.

In step 507 of FIG. 5, the process of detecting the target antigens 210 includes sweeping head module 104 with at least one magneto-resistive read sensor 108 over the sample assembly 100. In one embodiment head module 104 is moved linearly from left to right along the +Y axis relative to a stationary sample assembly. In another embodiment, the sample assembly 100 is swept linearly from right to left along the −Y axis past a stationary head module 104. If substrate 199 is of a flexible polyethylene terephthalate material, then in one embodiment, this right-to-left motion may be performed as data read-write operations in a magnetic tape drive. The head module 104 may sample a single sample trench 180, or simultaneously sample a plurality of sample trenches 180. As an alternate embodiment, head module 104 comprises a helical-scan rotary head module, and the Y-axis of the sample trench 180 is at an angle to the substrate 199. In this embodiment the sample trenches 180 are much shorter in length such that alignment of the head module 104 with sample trenches 180 may be accomplished without alignment marks 193. In one embodiment the IBM® MSS 3850 helical-scan tape drive may be utilized to detect analytes.

In one embodiment, the head module 104 comes into physical contact with the upper surface 254 of the outer layer 253 during the sweeping step of 507. Keeping the head module 104 in physical contact with the upper surface ensures that the head module 104 is kept at a known Z-axis position and assists with alignment of head module 104 with sample trenches 180. As discussed above, the outer layer 253 may comprise diamond-like-carbon, polytetrafluoroethylene, aluminum oxide, polyamides, or other low-friction materials known in the art. Accordingly, the low friction material of the outer layer assists the head module 104 to smoothly sweep the sample trenches 180 while in physical contact with the upper surface 254 of outer layer 253, such that the target antigens of the biological sample is reliably and accurately detected.

As discussed with respect to step 501 in FIG. 5, in some embodiments, the inner core 216 of nanoparticles are demagnetized. Accordingly, in this embodiment, as part of step 506, write-head 106 writes to nanoparticles 212 to magnetize inner cores 216 of nanoparticles if they are not already magnetized. Write-head 106 writes with a constant DC magnetic polarity for the duration of the sweeping step 506, such that there are no unwritten regions of sample assembly 100. In one embodiment, write-head 106 writes with magnetically-overlapping write pulses. Further in step 507, read-sensor 108 detects the freshly magnetized inner cores 216 of nanoparticles 212, and thus detects target antigens 210. Read-sensor can detect the target antigens 210 because nanoparticles 212 are bonded to antibodies 208B, which in turn are bonded to target antigens 210.

Write head 106 magnetizes inner cores 216 of nanoparticles 212 along the Y-axis, which is the longitudinal direction of recording in the tape drive industry. Read-sensor 108 magnetically detects nanoparticles 212 along the Y-axis. As a result in step 506, the nanoparticles 212 may be magnetized by write-head 106 and then immediately and magnetically detected by read-sensor 108 during a single sweep of the sample trenches 180. As discussed above, this process is referred to as a read-after-write operation. In one embodiment, the write-head 106 and read-sensor 108 are separated by a magnetic shield (not shown) to prevent cross-talk between write-head 106 and read-sensor 108 during step 507.

Alternatively, the steps of magnetizing nanoparticles 212 and the step of detecting the nanoparticles 212 may be performed separately. For example, write head 106 magnetizes inner cores 216 of nanoparticles 212 along the Y-axis of sample assembly 100. In one embodiment, write-head 106 is then turned off. Subsequently, read-sensor 108 magnetically detects nanoparticles 212 along the Y-axis. The read module sensor 108 may be swept across sample trenches 180 along the Y-axis in both the +Y and −Y directions. Accordingly, read-sensor 108 can repeatedly check for magnetized nanoparticles 212, thus ensuring that all target antigens 210 are detected.

In an embodiment in which the number of sample trenches 180 are greater than the number of write-head 106 and read-sensor 108 pairs in head module 104, the head module 104 may scan the sample trenches 180 in a serpentine fashion. The head module 104 performs a scan in the +Y direction, as head module 104 only provides read-after-write capability in the +Y direction as shown in FIG. 1. Then, a second head module (not shown) comprising a mirror image of head module 104, conducts a read-after-write operation in the −Y direction.

The coercivity of a magnetic inner core 216 may be chosen selectively depending upon the target antigen 210 to be detected. For example, nanoparticles 212 with magnetic inner cores 216 of different coercivity values may be respectively bonded to different types of antibodies 208A and 208B to detect various types of target antigens 210 on the sample assembly 100 simultaneously. Nanoparticles 212 may have different magnetic properties associated with each antigen-antibody combination. Read-sensor 108 detects the different magnetic properties of an inner core 216 based on the materials used for that inner core 216. As discussed above, magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality. As a result, in step 507, read-sensor 108 may detect more than one type of target antigens 210 with a single sweep of the sample assembly 100.

Figure 10:
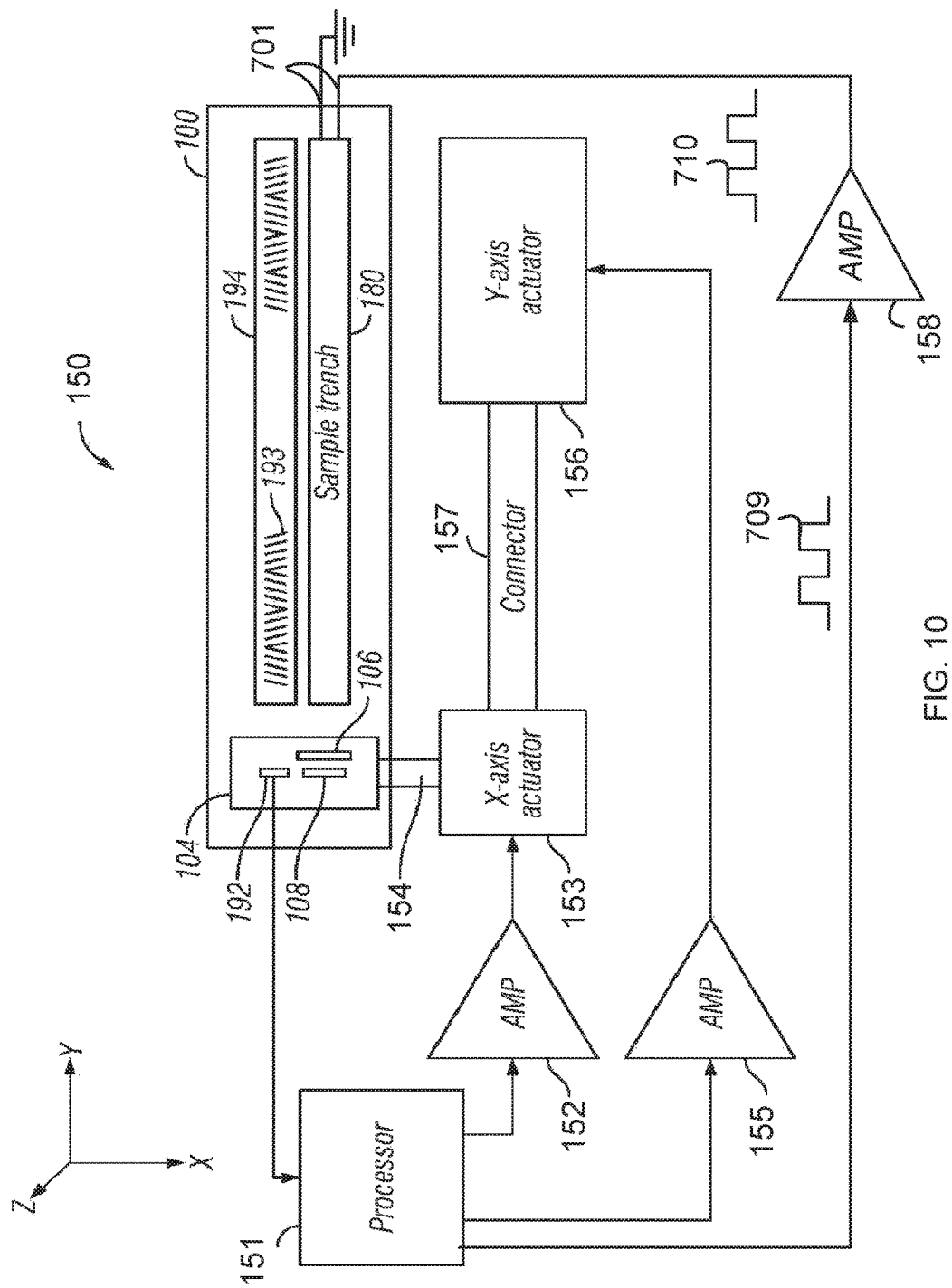
FIG. 10 illustrates a control circuit for the X-axis and Y-axis motion of the head module in an embodiment of the invention, and the application of an electrical current to an electric conductor for the generation of an electromagnetic field.

FIG. 10 illustrates an embodiment of a servo control system 150 for controlling the motion of head module 104 in the X-axis and Y-axis. For simplicity, FIG. 10 illustrates sample assembly 100 including a single trench 180. In addition, FIG. 10 shows a head module 104 including a single write-head 106 and read-sensor 108 pair and a PES read head 192. However, it should be understood that the sample assembly 100 may include a plurality of trenches and the head module 104 may include a plurality of write-heads 106 and read sensors 108. PES read-head 192 reads servo-alignment marks 193 in servo track 194. Processor 151 receives position-error-servo (PES) signals from PES read-head 192. Processor 151 sends a control signal to power amplifier 152 to control X-axis actuator 153 based on the PES information. In turn, the X-axis actuator 153 controls the motion of head module 104 in the X-axis direction. X-axis actuator 153 is connected to head module 104 via mechanical connector 154. Accordingly, head module 104 can be positioned to center write-head 106 and read-sensor 108 on sample trenches 180 of sample assembly 100. Processor 151 also sends control signals to power amplifier 155 to control Y-axis actuator 156 for conducting a scan by head module 104 across sample assembly 100. Y-axis actuator 156 is connected to X-axis actuator via mechanical connector 157, such that head module 104 can be moved along the Y-axis in a controllable manner.

Additionally, FIG. 10 illustrates an embodiment of applying current 702 through conductor 701. Processor 151 sends a low-power waveform-signal 709 to power-amplifier 158, which provides current 702. Current 702 flows through conductor 701 to ground, which is the return path for current 702 back to amplifier 158. Current 702 may be a DC steady-state current of a specific amperage. Alternately, current 702 may be a pulse-width-modulated (PWM), a square-wave current 710 (as shown in FIG. 10) which is a 50% duty-cycle PWM current, a triangular-waveform current of increasing amperage, a triangular-waveform current of decreasing amperage, and the like. In one embodiment, read sensor 108 measures the strength of the generated B field and provides feedback to processor 151 so that the current 702 can be adjusted accordingly.

Figure 11:
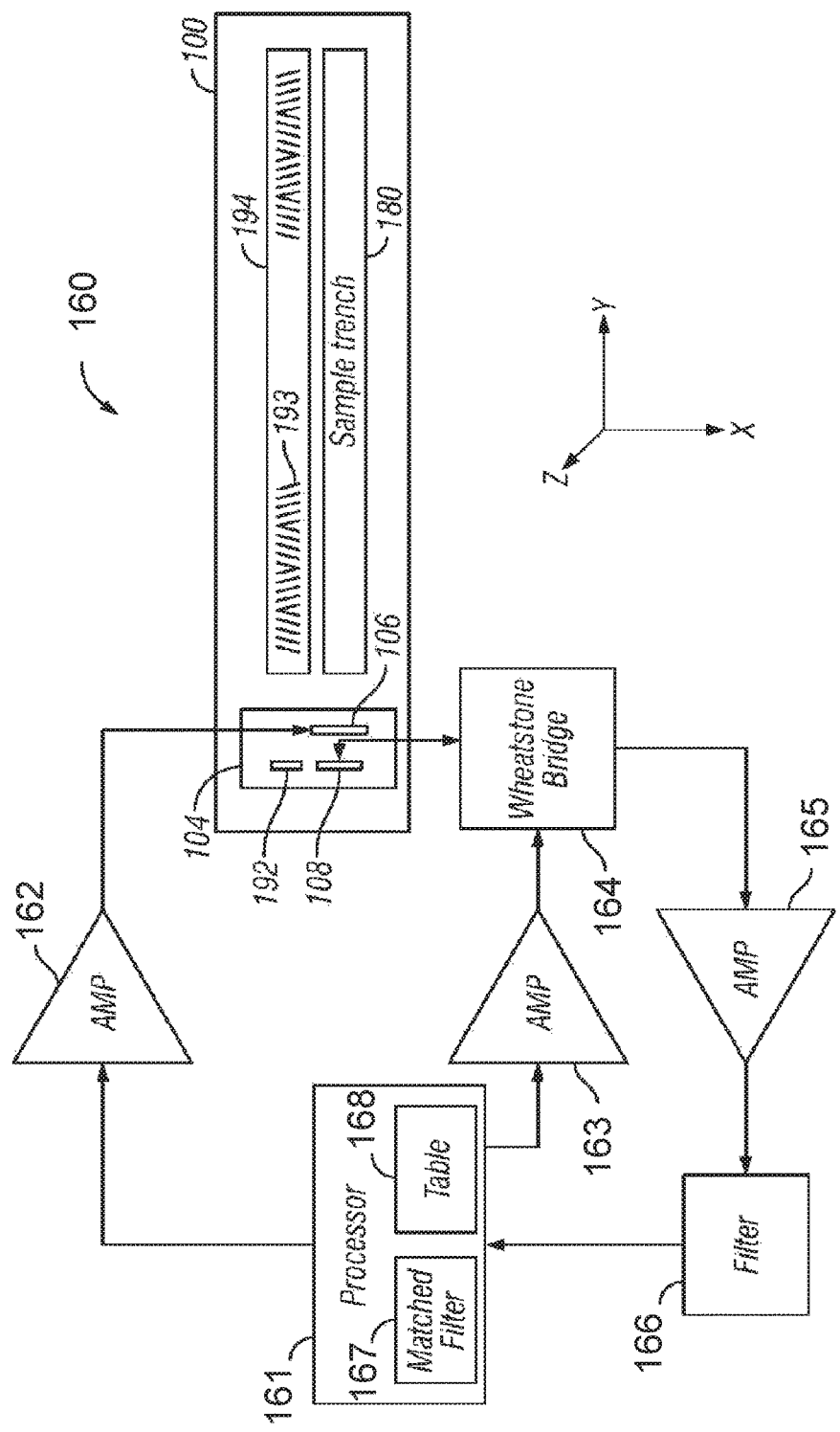
FIG. 11 illustrates read and write circuitry in an embodiment of the invention.

FIG. 11 illustrates one embodiment of a write and read circuitry 160 for use in writing to the sample trenches 180 (i.e, magnetizing nanoparticles 212) and reading from the sample trenches 180 (i.e, sensing and detecting the magnetized nanoparticles 212). For simplicity, FIG. 11 illustrates sample assembly 100 including a single trench 180. In addition, FIG. 11 shows a head module including a single write-head 106 and read-sensor 108 pair. However, it should be understood that the sample assembly 100 may include a plurality of trenches and the head module 104 may include a plurality of write-heads 106 and read sensors 108.

Processor 161 sends control signals to power amplifier 162. Power amplifier 162 provides power to write-head 106 for magnetizing nanoparticles 212. Processor 161 also sends control signals to power amplifier 163. Power amplifier 163 powers Wheatstone bridge 164. In one embodiment, Wheatstone bridge 164 includes read-sensor 108. Thus, read-sensor receives DC current from the Wheatstone bridge 164. Read-sensor 108 detects a resistance change during step 507 discussed above. The resistance change is based on the magnetic field provided by the magnetized inner cores 216 of nanoparticles 212. Wheatstone bridge 164 balances out the zero-magnetism resistance of read-sensor 108 such that only the change in resistance of read-sensor 108 is sent to amplifier 165. The amplifier 165 receives the change in resistance and sends the change in resistance to processor 161 through filter 166. Filter 166 filters out noise. In one embodiment, filter 166 filters out 60 Hz noise which is the type of noise that is pervasive in an office or laboratory setting in which processes of the invention may be performed.

Processor 161 includes a matched filter 167 and a table 168. Processor 161 determines if a nanoparticle 212 was detected, and thus, if a target antigen 210 has been detected. The change in resistance of read-sensor 108 is directly proportional to the magnetic field provided by nanoparticle 212. The change in resistance of read-sensor 108 is directly proportional to the magnetic field provided by nanoparticle 212.

As discussed above, the coercivity of a magnetic inner core 216 may be chosen selectively depending upon the target antigen 210 to be detected. For example, nanoparticles 212 with magnetic inner cores 216 of different coercivity values may be respectively bonded to different types of antibodies 208A and 208B to detect various types of target antigens 210 on the sample assembly 100 simultaneously. The identification of the target antigens 210 in the sample trenches 180 may be facilitated by a lookup table 168 in processor 161. In one embodiment, the lookup table 168 includes a list of (a) target antigens 210, (b) the antibodies 208A and 208B bonded with the target antigens 210, and (c) the coercivity of the inner cores 216 of nanoparticles 212 bonded to antibodies 208B.

In one embodiment of the invention, a correlation calculation is performed by the write and read circuit of FIG. 11 to improve the detection accuracy of target antigens. The processor 161 performs correlation calculation C(y) shown in equation [1] between a detection signal profile g(y) read by read-sensor 108 when a nanoparticle 212 is detected and a matched filter 167.

$$C(y)=\int g(\eta)h(\eta-y)d\eta \qquad \text{Equation [1]}$$

In equation [1], $\eta$ is the integration variable along the Y-axis that varies as read-sensor 108 sweeps along the Y-axis. The matched filter 167 includes an impulse response h(y) of an ideal signal profile of a detected target nanoparticle 212. Since h(y) is used repetitively, it may be calculated once and stored as matched filter 167 in processor 161.

The range of correlation C(y) is between −1 and +1, where +1 represents an ideal correlation of one hundred percent (100%), and −1 indicates no correlation. The electrical waveform g(y) of each potential detection of a nanoparticle 212 by read-sensor 108 has its correlation C(y) calculated in step 507 of FIG. 5. Processor 161 then compares this correlation C(y) against a threshold correlation value C0 before accepting the signal g(y) as a valid detection of a nanoparticle 212. This correlation removes spurious electrical noise from actual detections of nanoparticles, and thus reduces false-positive detections of target antigens 210.

In one embodiment, the results of the sweep of step 507 may be displayed to a physician or clinician to inform the physician or clinician of the presence (or absence) of target antigens 210 in the biological sample. The results may include items such as the target antigen(s) tested for, the types of antibodies used, a simple positive-detection or negative-detection indication for each antigen, the number of nanoparticles detected for each antigen to give an indication of the prevalence of the targeted antigen, and the number of rejected detections based on the correlation calculation.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries. Additionally, a description of an embodiment with several components in communication with each other does not imply that all such components are required. On the contrary a variety of optional components are described to illustrate the wide variety of possible embodiments.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

While particular embodiments of the present invention have been shown and described, it will be obvious to those skilled in the art that, based upon the teachings herein changes and modification may be made without departing form this invention and its broader aspects and, therefore, the appended claims are to encompass within their scope all such changes and modifications as are within the true spirit and scope of this invention. Furthermore, it is to be understood that the invention is solely defined by the appended claims.

What is claimed is:

1. A sample assembly comprising:
a substrate;
a first portion of an outer layer, wherein the first portion of the outer layer is formed above the substrate;
a second portion of the outer layer, wherein the second portion of the outer layer is formed above the substrate;
one or more base layers formed between the substrate and the first and second portions of the outer layer;
a sample trench formed above the one or more base layers and between the first and second portions of the outer layer, the sample trench being characterized by a bottom surface, and a longitudinal axis;
an electrical conductor disposed in the substrate, the electrical conductor being configured to generate an electromagnetic field in proximity to the sample trench to enhance nanoparticle movement toward the bottom surface of the sample trench; and
at least one alignment trench formed above the substrate, each alignment trench having a longitudinal axis substantially parallel to a longitudinal axis of the sample trench, and each alignment trench being a separate structure from the sample trench,
wherein each alignment trench comprises a plurality of markings configured to facilitate alignment of an electromagnetic write head of a magnetic tape drive with the sample trench, and wherein the markings are non-magnetic markings.

2. The sample assembly of claim 1, further comprising: a biological sample in the sample trench, the biological sample comprising:
a first set of antibodies bonded to the sample assembly via the bottom surface of the sample trench;
one or more target antigens; and
a second set of antibodies, wherein the second set of antibodies are bound to the nanoparticles,
wherein the second set of antibodies are characterized by binding with the target antigens, and
wherein each of the first and second sets of antibodies are biologically identical.

3. The sample assembly of claim 2, wherein the nanoparticles are bound to the target antigens.

4. The sample assembly of claim 1, wherein the electrical conductor is entirely disposed below a substrate surface, and wherein the electrical conductor comprises a material selected from gold, copper, aluminum and silver.

5. The sample assembly of claim 1, further comprising an external magnet not physically coupled to the sample assembly,
wherein the external magnet is located in proximity to the sample assembly, wherein the external magnet is positioned to increase a magnitude of the electromagnetic field and further facilitate the nanoparticle movement toward the bottom surfaces of the sample trench.

6. The sample assembly of claim 1, the at least one alignment trench comprising a plurality of the alignment trenches, wherein each alignment trench is formed in either the first portion of the outer layer or the second portion of the outer layer.

7. The sample assembly of claim 1, wherein the nanoparticles are magnetized.

8. The sample assembly of claim 1, wherein the sample trench and the at least one alignment trench are each characterized by a substantially linear shape.

9. The sample assembly of claim 1, the outer layer comprising one or more materials selected from the group consisting of:
silicon dioxide, aluminum oxide ($Al_2O_3$), diamond-like carbon (DLC), and combinations thereof.

10. The sample assembly of claim 1, the sample trench being substantially linear along a longitudinal axis thereof.

11. The sample assembly of claim 1, wherein the one or more base layers are arranged in a single layer formed directly on the substrate.

12. The sample assembly of claim 1, comprising a plurality of the alignment trenches, wherein each alignment trench:
has a longitudinal axis, and a substantially linear shape arranged along the longitudinal axis thereof;
is formed adjacent to the sample trench; and
is parallel to the longitudinal axis of the sample trench.

13. A method of forming a sample assembly of a biological sample having target antigens, the method comprising:
providing a substrate having a surface and an embedded electrical conductor;
bonding a first set of antibodies on the substrate surface;

exposing the substrate surface with the first set of bonded antibodies to the biological sample having the target antigens, wherein the target antigens bond with the first set of antibodies on a bottom surface of each of a plurality of sample trenches, each sample trench having a substantially linear shape and being formed in an outer layer disposed above the substrate, at least some of the sample trenches being in proximity to one or more alignment trenches having a longitudinal axis substantially parallel to a longitudinal axis of the proximate sample trench, and each alignment trench comprising markings configured to facilitate alignment of an electromagnetic write head of a magnetic tape drive;

bonding a second set of antibodies to nanoparticles, wherein the first and second sets of antibodies are biologically identical;

exposing the target antigens bonded with the first set of antibodies to the second set of antibodies bonded with the nanoparticles, wherein the second set of antibodies bond with the target antigens; and applying an electric current through the electrical conductor to generate an electromagnetic field, wherein the electromagnetic field generated by applying the electric current through the electrical conductor comprises an electrical component and a magnetic component, wherein the magnetic component of the electromagnetic field moves the nanoparticles toward the bottom surface of the plurality of sample trenches, and wherein moving the nanoparticles toward the bottom surface of the plurality of sample trenches speeds up the bonding between the second set of antibodies and the target antigens.

14. A method of detecting target antigens in a biological sample on a sample assembly, the sample assembly including a substrate having a surface and an electrical conductor, the method comprising:

bonding a first set of antibodies on the substrate surface exposed via one or more sample trenches formed in an outer layer positioned above the substrate surface, each sample trench having a longitudinal axis and a substantially linear shape arranged along the longitudinal axis thereof, at least one of the sample trenches being in proximity to one or more alignment trenches having a longitudinal axis substantially parallel to the longitudinal axis of the proximate sample trench, and each alignment trench comprising markings configured to facilitate alignment of an electromagnetic write head of a magnetic tape drive;

exposing the substrate surface with the first set of bonded antibodies to the biological sample having the target antigens, wherein the target antigens bond with the first set of antibodies;

bonding a second set of antibodies to nanoparticles, wherein the first and second sets of antibodies are biologically identical;

exposing the target antigens bonded with the first set of antibodies to the second set of antibodies bonded with the nanoparticles, wherein the second set of antibodies bond with the target antigens;

applying an electric current through the electrical conductor to generate an electromagnetic field, wherein the electromagnetic field generated by applying the electric current through the electrical conductor comprises an electrical component and a magnetic component, wherein the magnetic component of the electromagnetic field moves the nanoparticles toward bottom surface of the one or more sample trenches, and wherein moving the nanoparticles toward the bottom surface of the one or more sample trenches speeds up the bonding between the second set of antibodies and the target antigens;

magnetizing the nanoparticles using an electromagnetic write head; and reading the magnetized nanoparticles using a magneto-resistive read sensor to detect the target antigens.

15. The method of claim 14, wherein the electromagnetic write head and the magneto-resistive read sensor are parts of a read-write head module in a data storage system.

16. The method of claim 14, further comprising bonding the first set of antibodies to the substrate surface and bonding the second set of antibodies to the nanoparticles using a material selected from the group consisting of amide, self-assembled-monolayers (SAMS), alkoxysilane, organic functional trialkoxysilane, and thiol.

17. The method of claim 14, further comprising aligning at least one of the electromagnetic write head and the electromagnetic read sensor with at least one of the sample trenches using at least one alignment trench also formed in the outer layer, each alignment trench having a longitudinal axis and a substantially linear shape arranged along the longitudinal axis thereof.

18. The method of claim 17, wherein the at least one alignment trench and the one or more sample trenches are substantially parallel along the longitudinal axes thereof.

19. The method of claim 14, wherein applying the electromagnetic field through the electrical conductor to generate the electromagnetic field moves the nanoparticles toward the sample surface at a rate about two orders of magnitude greater than a rate at which the nanoparticles move toward the sample surface in absence of applying the electrical current through the electrical conductor to generate the electromagnetic field.

* * * * *